(12) United States Patent
Kaupp et al.

(10) Patent No.: US 11,299,636 B2
(45) Date of Patent: Apr. 12, 2022

(54) EFFECT PIGMENTS BASED ON ARTIFICIALLY PRODUCED SUBSTRATES WITH A NARROW SIZE DISTRIBUTION

(75) Inventors: Günter Kaupp, Neuhaus (DE); Ulrich Schmidt, Hersbruck (DE); Dirk Schumacher, Pegnitz (DE); Ralph Schneider, Lauf (DE)

(73) Assignee: Eckart GmbH, Hartenstein (DE)

( * ) Notice: Subject to any disclaimer, the term of this patent is extended or adjusted under 35 U.S.C. 154(b) by 94 days.

(21) Appl. No.: 12/864,146

(22) PCT Filed: Nov. 25, 2008

(86) PCT No.: PCT/EP2008/009993
§ 371 (c)(1),
(2), (4) Date: Jul. 22, 2010

(87) PCT Pub. No.: WO2009/103322
PCT Pub. Date: Aug. 27, 2009

(65) Prior Publication Data
US 2010/0297045 A1    Nov. 25, 2010

(30) Foreign Application Priority Data
Feb. 20, 2008   (EP) .................................... 08003114

(51) Int. Cl.
| | | |
|---|---|---|
| *A61K 8/25* | (2006.01) | |
| *C09C 1/00* | (2006.01) | |
| *A61K 8/02* | (2006.01) | |
| *A61Q 1/02* | (2006.01) | |
| *C08K 9/02* | (2006.01) | |
| *A61K 8/19* | (2006.01) | |
| *C09D 5/36* | (2006.01) | |
| *A61Q 1/06* | (2006.01) | |
| *A61Q 19/10* | (2006.01) | |
| *A61Q 1/04* | (2006.01) | |
| *A61Q 1/10* | (2006.01) | |
| *A61Q 19/00* | (2006.01) | |
| *A61Q 17/04* | (2006.01) | |
| *A61Q 3/02* | (2006.01) | |
| *A61Q 1/08* | (2006.01) | |
| *A61Q 1/12* | (2006.01) | |
| *A61Q 13/00* | (2006.01) | |

(52) U.S. Cl.
CPC .......... *C09C 1/0015* (2013.01); *A61K 8/0229* (2013.01); *A61K 8/0266* (2013.01); *A61K 8/19* (2013.01); *A61K 8/25* (2013.01); *A61Q 1/02* (2013.01); *C08K 9/02* (2013.01); *C09C 1/0018* (2013.01); *C09C 1/0021* (2013.01); *C09C 1/0024* (2013.01); *C09D 5/36* (2013.01); *A61K 2800/412* (2013.01); *A61K 2800/436* (2013.01); *A61K 2800/621* (2013.01); *A61K 2800/651* (2013.01); *A61Q 1/04* (2013.01); *A61Q 1/06* (2013.01); *A61Q 1/08* (2013.01); *A61Q 1/10* (2013.01); *A61Q 1/12* (2013.01); *A61Q 3/02* (2013.01); *A61Q 13/00* (2013.01); *A61Q 17/04* (2013.01); *A61Q 19/00* (2013.01); *A61Q 19/10* (2013.01); *C01P 2004/51* (2013.01); *C09C 2200/102* (2013.01); *C09C 2200/1004* (2013.01); *C09C 2200/1062* (2013.01); *C09C 2200/1087* (2013.01); *C09C 2200/301* (2013.01); *C09C 2200/304* (2013.01); *C09C 2220/10* (2013.01); *C09C 2220/106* (2013.01)

(58) Field of Classification Search
None
See application file for complete search history.

(56) References Cited

U.S. PATENT DOCUMENTS

| | | | |
|---|---|---|---|
| 989,671 | A | 4/1911 | Voelker |
| 3,331,699 | A | 7/1967 | Marshall et al. |
| 4,128,435 | A | 12/1978 | Bäumer et al. |
| 5,017,207 | A | 5/1991 | Watkinson et al. |
| 5,156,889 | A | 10/1992 | DeLuca, Jr. |
| 5,436,077 | A | 7/1995 | Matsuba et al. |
| 5,540,769 | A * | 7/1996 | Franz ................ C09C 1/0015 106/415 |

(Continued)

FOREIGN PATENT DOCUMENTS

| | | |
|---|---|---|
| EP | 0 289 240 B1 | 11/1988 |
| EP | 1 142 962 A1 | 10/2001 |

(Continued)

OTHER PUBLICATIONS

Heinrich Zollinger, Color Chemistry, synthesis, properties, and applications of organic dyes and pigments, 2003, Verlag Helvetica Chimica Acta, third edition revised, pp. 416-420.*

(Continued)

*Primary Examiner* — Jake M Vu
(74) *Attorney, Agent, or Firm* — Fitch, Even, Tabin & Flannery, L.L.P.

(57) ABSTRACT

The invention relates to effect pigments comprising artificial platelet-shaped substrates which have at least one optically active coating, where the effect pigments have a volume-averaged cumulative undersize distribution curve with the characteristic numbers $D_{10}$, $D_{50}$ and $D_{90}$, said cumulative undersize distribution curve having a span $\Delta D$ of 0.7-1.4, and the span $\Delta D$ being calculated in accordance with formula (I):

$$\Delta D = (D_{90} - D_{10})/D_{50} \qquad (I),$$

and the average thickness of the artificial platelet-shaped substrates being 500 nm to 2000 nm.

14 Claims, 3 Drawing Sheets

(56) References Cited

U.S. PATENT DOCUMENTS

| | | | |
|---|---|---|---|
| 6,045,914 | A | 4/2000 | Sullivan et al. |
| 6,630,018 | B2 | 10/2003 | Bauer et al. |
| 6,645,286 | B2 | 11/2003 | Ostertag et al. |
| 6,914,656 | B2 | 7/2005 | Sakamoto et al. |
| 7,604,862 | B2 | 10/2009 | Ambrosius et al. |
| 7,691,196 | B2 | 4/2010 | Pfaff et al. |
| 8,946,340 | B2 | 2/2015 | Yagyu et al. |
| 2003/0125416 | A1* | 7/2003 | Munro .................. C09D 5/004 523/171 |
| 2004/0221770 | A1 | 11/2004 | Schmidt et al. |
| 2005/0013934 | A1 | 1/2005 | Xiong et al. |
| 2005/0019575 | A1 | 1/2005 | Jungnitz et al. |
| 2005/0176850 | A1* | 8/2005 | Schmidt .............. C09C 1/0015 523/160 |
| 2006/0042509 | A1 | 3/2006 | Henglein et al. |
| 2006/0225609 | A1 | 10/2006 | Rueger et al. |
| 2007/0032573 | A1 | 2/2007 | Yanagase et al. |
| 2007/0066719 | A1* | 3/2007 | Xia ........................ C08J 3/226 523/205 |
| 2007/0134179 | A1 | 6/2007 | Ino et al. |
| 2007/0199478 | A1 | 8/2007 | Schlegl et al. |
| 2009/0258251 | A1 | 10/2009 | Abe et al. |
| 2009/0274735 | A1 | 11/2009 | Wakamiya |
| 2010/0116169 | A1* | 5/2010 | Kaupp et al. ............... 106/31.9 |

FOREIGN PATENT DOCUMENTS

| | | |
|---|---|---|
| EP | 1 865 032 A2 | 12/2007 |
| EP | 2 009 066 A1 | 12/2008 |
| JP | S45-3541 | 2/1970 |
| JP | H09-77637 A | 3/1997 |
| JP | 2000-281932 | 10/2000 |
| JP | A-2000-319540 A | 11/2000 |
| JP | 2002-363440 A | 12/2002 |
| JP | 2005-502738 | 1/2005 |
| JP | A-2005-502738 A | 1/2005 |
| JP | 2005-042112 | 2/2005 |
| JP | 2006-212478 A | 8/2006 |
| JP | 2006-522192 | 9/2006 |
| JP | 2007-126643 | 5/2007 |
| JP | 2007-327059 | 12/2007 |
| JP | 41-17148 | 4/2008 |
| JP | 2008-174698 | 7/2008 |
| JP | A-2008-174698 | 7/2008 |
| JP | 2008-534753 | 8/2008 |
| KR | 10-0253774 | 5/2000 |
| KR | 10-2004-0084998 | 10/2004 |
| KR | 10-2006-0090226 | 8/2006 |
| WO | WO 97/29059 | 8/1997 |
| WO | WO 2002/090448 A2 | 11/2002 |
| WO | WO 03/006558 A2 | 1/2003 |
| WO | WO 2004/055119 A1 | 7/2004 |
| WO | WO 2005/063637 A1 | 7/2005 |
| WO | WO 2006/021386 A1 | 3/2006 |
| WO | WO 2006/110359 A2 | 10/2006 |
| WO | WO 2006/110359 A3 | 10/2006 |
| WO | WO 2007/111221 A1 | 10/2007 |
| WO | WO 2007/114442 A1 | 10/2007 |
| WO | WO 2008/122420 A1 | 10/2008 |

OTHER PUBLICATIONS

Horiba (https://www.horiba.com/fileadmin/uploads/Scientific/eMag/PSA/Guidebook/pdf/PSA_Guidebook.pdf(2017)) (Year: 2017).*

Wikipedia (https://en.wikipedia.org/wiki/Anatase downloaded on Jan. 25, 2021) (Year: 2021).*

International Search Report dated Jul. 30, 2009, issued in corresponding international application No. PCT/EP2008/009993.

European Search Report dated Aug. 11, 2008, issued in corresponding European priority application No. EP 08003114.

Summary of Examples described in WO 2007/114442 A1 (EP 2 009 066 A1) (1 page).

"Titanium Dioxide, There is Still No Substitute for Opacity, Titanium DiOxide is the Key!" by Kalamazoo Paper Chemicals, A Division of JOYCECO Inc. retrieved from http://www.kalpaperchem.com/titan.htm, 1998-2011 (2 pages).

Product Specifications & Properties Sheet as published in 2007 by BASF Corporation for Reflecks™ Dimensions Luminous White (Product No. G130M) (1 page).

"Pearlescent and Iridescent Pigments and Colors for Color Cosmetics and Personal Care Products," Technical Information Sheet published in Aug. 2008 by BASF Corporation for Reflecks™ product range (12 pages).

BASF Corporation Bill of Lading No. 2093793369 issued on Sep. 20, 2007 for customer's (Autumn Harp Inc.) purchase of identified pigment products (2 pages).

BASF Corporation Invoice No. 3092918397 issued on Sep. 20, 2007 to customer (Autumn Harp Inc.) for purchase of identified pigment products (3 pages).

Third party submission (Eckart GmbH) regarding EP 06758255.1-1218 of BASF Catalysts LLC dated Feb. 14, 2012 (with English translation) (27 total pages).

Engelhard, product brochure Firemist®, special effect pigments, 2003 (4 pages).

Engelhard, product brochure Firemist®, special effect pigments, 2004 (4 pages) (cited in Third party submission (Eckart GmbH) regarding EP 06758255.1-1218 above).

BASF Effect Pigments Technical Data Sheet: Firemist® Super Pearl 9G130M, May 2010 (3 pages).

BASF Effect Pigments Technical Data Sheet: Firemist® Super Gold 9G230M, May 2010 (3 pages).

BASF Effect Pigments Technical Data Sheet: Firemist® Super Red 9G430M, May 2010 (3 pages).

BASF Effect Pigments Technical Data Sheet: Firemist® Super Blue 9G630M, May 2010 (3 pages).

Dr. Adalbert Huber, et al., "Special Effect Pigments," Merck KGaA, division pigments, Phaenomen Farbe Mar. 2005, pp. 34-36 (with English translation).

Xirallic®, T60-10 SW Crystal Silver for Coatings Product Information, Merck, Publication Apr. 2006 (4 pages).

Schulz et al., "Star Effects of Borosilicate, New Developments on Borosilicate Based Interference Pigments," 23rd IFSCC Congress, Orlando 2004 (2 pages).

European Office Action dated Aug. 24, 2008 in counterpart European Patent Application No. 11 171 703.9.

Office Action dated Apr. 5, 2013 in U.S. Appl. No. 13/131,671.

Notice of Reasons for Rejection dated Oct. 30, 2012 in corresponding Japanese Patent Application No. 2010-547050.

Notice of Reasons for Rejection dated Dec. 3, 2013 in corresponding Japanese Patent Application No. 2012-525071 (with English language translation).

Notice of Reasons for Rejection dated Dec. 3, 2013 in corresponding Japanese Patent Application No. 2012-525072 (with English language translation).

Notice of Reasons for Rejection dated Nov. 10. 2015 in corresponding Japanese Patent Application No. 2010-547050 (Appeal No. 2014-6188) with English language translation (7 total pages).

Non-patent literature reference Notice of Reasons for Rejection dated Nov. 10, 2015, Kagaku-daijiten (a dictionary of science) $2^{nd}$ version edited by Zaidanhoujin-Kokusai-Kagaku-sinkouzaidan and issued from Maruzen Kabushikikaisha on Feb. 28, 2005, pp. 1265, 139, 1351 and 856.

BASF Corporation's Bill of Lading No. 2093943188 as issued on Nov. 3, 2007 for customer's purchase of 5 kg of Firemist® Super Pearl 9G130M (Lot No. 7F12F) (1 page).

BASF Corporation's Bill of Lading No. 2094056951 as issued on Jan. 29, 2008 for customer's purchase of 20 kg of Firemist® Super Pearl 9G130M (Lot No. 7K24F) (1 page).

Particle size distribution measurement dated Jan. 30, 2015 for sample of Firemist® Super Pearl 9G130M pigments (Lot No. 7I14F) using a Malvern MS 3000 (1 page).

BASF's Determination of Glass substrate thickness results dated Mar. 2, 2015 for sample of Firemist® Super Pearl 9G130M pigments (Lot No. 7I14F), incl. 3-page Excel data sheet (with English language translation)(11 pages).

(56) References Cited

OTHER PUBLICATIONS

Paul Kippax, "Why Particle Sizing?," Paint & Coatings Industry magazine, (2005), (with English translation) (total 11 pages).
Chemistry of Pigment, (1993), with English translation of p. 388, second paragraph (total 5 pages).
Ian Wheeler, Metallic Pigments in Polymers, (1999), with English translation (total 8 pages).
Product catalog 1 of a flaky glass substrate—MICROGLAS® C-Glass Flake—Nippon Sheet Glass Co., Ltd., received from Korean Examiner in corresponding Korean Application No. 10-2010-7020653 Apr. 25, 2017 (total 2 pages).
Product catalog 2 of a flaky glass substrate—MICROGLAS® Glass Flake, Nippon Sheet Glass Co., Ltd., http://www.frpservices.com/jp/composite/glass-flake.html http://www.ngfeurope.com/~/media/NGF%20Europe/Site%20Content/Glass%20Flake/NGF%20Glass%20Flake.ashx, received from Korean Examiner in corresponding Korean Application No. 10-2010-7020653 Apr. 25, 2017 (total 7 pages).
Glass Fibre—Directory and Databook, Edition 2, ISBN 0412783703, (1997), p. 323.
Translation of communication dated Mar. 28, 2012 from Merck Patent GmbH to the European Patent Office regarding applicant's corresponding European Patent Application 08872586.6-EP 2 217 664 B1.
Translation of EP 2 217 664 B1, dated Jun. 29, 2011, claims as amended.
Translation of Sep. 29, 2014 communication under reference E/49184EPW/AW/kn from Patent Attorneys Louis Pöhlau Lohrentz to the European Patent Office regarding applicant's corresponding European Patent Application 08872586.6-EP 2 217 664 B1.
Translation of Nov. 21, 2012 communication under reference E/49184EPW/AW/pz from Patent Attorneys Louis Pöhlau Lohrentz to the European Patent Office regarding applicant's corresponding European Patent Application 08872586.6-EP 2 217 664 B1.
Translation of Sep. 29, 2014 communication from Merck Patent GmbH to the European Patent Office regarding applicant's corresponding European Patent Application 08872586.6-EP 2 217 664 B1.
Translation of Apr. 9, 2018 online filing under reference 49184EPW-BS/AW/pn by Patent Attorneys Louis Pöhlau Lohrentz to the European Patent Office regarding applicant's corresponding European Patent Application 08872586.6-EP 2 217 664 B1.
Translation of Annex to the Summons to attend oral proceedings communication of the opposition division dated Apr. 1, 2014 (Sheet 1 to Sheet 8) regarding applicant's corresponding European Patent Application 08872586.6-EP 2 217 664 B1.
Translation of Annex of the Grounds for decision of the interlocutory decision in opposition proceedings dated Dec. 3, 2014 (Sheet 1 to Sheet 12) regarding applicant's corresponding European Patent Application 08872586.6-EP 2 217 664 B1.
Translation of Aug. 26, 2015 communication under reference E/49184EPW/AW/en from Patent Attorneys Louis Pöhlau Lohrentz to the European Patent Office regarding applicant's corresponding European Patent Application 08872586.6-EP 2 217 664 B1.
Translation of communication from the Board of Appeal (preliminary decision) dated Jan. 12, 2018 under reference E/49184epw/AW regarding applicant's corresponding European Patent Application 08872586.6-EP 2 217 664 B1.
Translation of Jun. 7, 2018 communication of the Boards of Appeal incl. decision of the Boards of Appeal dated May 7, 2018 under reference E/49184epw/AW regarding applicant's corresponding European Patent Application 08872586.6-EP 2 217 664 B1.
Notice of Result of Reexamination for Reconsideration for Examiner before Appeal for Korean Application No. 10-2010-7020653 dated Jul. 10, 2015.
Trial Decision on Appeal Against Decision to Reject for Korean Application No. 10-2010-7020653 dated Oct. 24, 2016.
Trial Decision on Final Judgment on Revocation for Korean Application No. 10-2010-7020653 dated Aug. 31, 2017.
Written Decision on Registration for Korean Application No. 10-2010-7020653 dated Oct. 1, 2017.
Notice of Result of Reexamination for Reconsideration for Examiner before Appeal for Korean Application No. 10-2015-7014346 dated Jun. 7, 2016.
Trial Decision on Appeal Against Decision to Reject for Korean Application No. 10-2015-7014346 dated Dec. 22, 2017.
Written Decision on Registration for Korean Application No. 10-2015-7014346 dated Jan. 8, 2018.

\* cited by examiner

EFFECT PIGMENTS BASED ON ARTIFICIALLY PRODUCED SUBSTRATES WITH A NARROW SIZE DISTRIBUTION

CROSS REFERENCE TO RELATED APPLICATIONS

The present application is a 35 U.S.C. § 371 National Phase conversion of PCT/EP2008/009993, filed Nov. 25, 2008, which claims benefit of European Application No. 08003114.9, filed Feb. 20, 2008, the disclosure of which is incorporated herein by reference. The PCT International Application was published in the German language.

TECHNICAL FIELD

The present invention relates to new effect pigments which are based on artificial substrates and which feature improved optical properties.

BACKGROUND OF THE INVENTION

The present invention further relates to a new process for producing these effect pigments and also to their use in cosmetics, paints, printing inks, varnishes, powder coating materials, and plastics.

The optical effect of effect pigments is based on the directed reflection of light at predominantly planar, light-refracting pigment particles which are aligned substantially parallel to one another. These pigments particles generally have a substantially transparent substrate and one or more coatings on the substrate. Depending on the composition of the coating(s) of the pigment particles, interference, reflection, and absorption phenomena produce perceptions of color and lightness. Irregularities in the substrate surface to be coated, or colored impurities in the substrate, can lead to unwanted scattered-light effects or instances of unclean color in the end product. These unwanted scattered-light effects and/or color impurities occur particularly when natural substrate materials are used, such as natural mica. In circumventing the aforementioned drawbacks, artificial substrates afford new opportunities for high-quality pigments with new color and luster effects.

U.S. Pat. No. 3,331,699 A describes pearlescent pigments based on glass flakes with interference colors and an intense sparkle effect. The glass flakes are coated with a translucent metal oxide layer of high index. The color of the pigments is dependent on the selected metal oxide and on the thickness of the metal oxide layer.

The metal-coated glass flakes coated to counter corrosive effects with an additional protective layer of metal oxides such as $SiO_2$, $Al_2O_3$ or $TiO_2$ are described in U.S. Pat. No. 5,436,077 A. These coated glass flakes are comparable in terms of their appearance with metal foils.

Glass flakes coated with titanium oxides and/or iron oxides are known from U.S. Pat. No. 6,045,914 A. The average particle size of the glass flakes is situated in a range from approximately 1 to 250 µm, the thickness being around 0.1 to 10 µm.

WO 2004/055119 A1 describes interference pigments which are based on coated platelet-shaped substrates. The substrates in this case are covered with a first layer of $SiO_2$ to which is applied subsequently a high-index layer consisting, for example, of $TiO_2$, $ZrO_2$, $SnO_2$, $Cr_2O_3$, $Fe_2O_3$ or $Fe_3O_4$, or an interference system comprising alternating high-index and low-index layers. Optionally the pigments may further have an outer protective layer.

Thermally and mechanically stable, metal oxide-coated effect pigments based on thin glass flakes with a thickness ≤ 1.0 µm are known from WO 2002/090448 A2.

The optical properties of effect pigments can be influenced, in accordance with WO 2006/110359 A2, by an appropriate particle size distribution. The classified, metal oxide-coated glass flakes described therein have a $D_{10}$ of at least 9.5 µm, preferably of 9.5 µm. A drawback is that the pigments have to have a size range with a $D_{90}$ value of not more than 85 µm, preferably of about 45 µm. Consequently, in accordance with the teaching of WO 2006/110359 A2, only small-particle effect pigments with enhanced sparkle effect can be provided.

Performance drawbacks, such as the clogging of filters, for example, can be prevented in accordance with the teaching of WO 2007/114442 A1 by an appropriate particle size distribution, in which the $D_{10}$ is between 4.7 and 25 µm and the ratio of $D_{90}$ to $D_{10}$ is between 2 and 3.

A drawback of the effect pigments known to date in the prior art is that their color purity is low. Hence a viewer viewing a plurality of effect pigments from one batch under a light microscope will see effect pigments having a variety of colors—that is, colors which are different from one another.

SUMMARY

It is an object of the present invention to provide new effect pigments having improved optical properties, more particularly having a color purity which is increased relative to the prior art, at a constant angle of light incidence and angle of viewing. It is a further object of the invention to provide a process for producing these effect pigments.

This object has been achieved by a provision of effect pigments comprising artificial platelet-shaped substrates which have at least one optically active coating, where the effect pigments have a volume-averaged cumulative undersize distribution curve with the characteristic numbers $D_{10}$, $D_{50}$ and $D_{90}$, said cumulative undersize distribution curve having a span ΔD of 0.7-1.4, and the span ΔD being calculated in accordance with formula (I):

$$\Delta D = (D_{90} - D_{10})/D_{50} \qquad (I),$$

and the average thickness of the artificial platelet-shaped substrates being 500 nm to 2000 nm.

Preferred developments are specified in dependent claims 2 to 10.

The object has further been achieved through the provision of a process for producing the effect pigments of the invention, comprising the following steps:
a) size-classifying the artificial substrates,
b) coating the artificial substrates.

The coating of substrates in step b) takes place preferably after the size-classifying in step a).

Further provided by the invention is the use of the effect pigments of the invention in cosmetics, plastics, and coating compositions, such as paints, printing inks, varnishes, powder coating materials, and electrocoat materials. The invention accordingly provides compositions which comprise the effect pigments of the invention.

DETAILED DESCRIPTION OF CERTAIN EMBODIMENTS

Effect pigments having improved optical properties are, for the purposes of this invention, effect pigments notable in particular for their high color purity at a constant angle of light incidence and angle of viewing. In their respective entirety, then, the effect pigments of the invention have a uniform color or a uniform hue. For a viewer, therefore, there are no marked color differences from one effect pigment of the invention to the next effect pigment of the invention in an entirety.

Surprisingly it has been found that substrates having a narrow span in the particle size distribution and coated with at least one optically active coating exhibit a markedly higher color purity than effect pigments having a broader span, as is the case in the prior art.

The invention characterizes the particle size distribution using the span $\Delta D$, defined as $\Delta D=(D_{90}-D_{10})/D_{50}$. The smaller the span, the narrower the particle size distribution.

The $D_{10}$ value indicates the value of the longitudinal dimension of the effect pigments, as determined by means of laser granulometry in the form of the sphere equivalent, which 10% of the pigment particles attain at most, or fall below, out of the entirety of all the particles. Correspondingly, the $D_{50}$ value and the $D_{90}$ value, respectively, indicate the maximum longitudinal dimensions of the effect pigments, as determined by means of laser granulometry in the form of sphere equivalents, which 50% or 90% of the particles attain at maximum, or fall below, out of the entirety of all the particles.

The effect pigments of the invention possess a span $\Delta D$ in a range from 0.7 to 1.4, preferably from 0.7 to 1.3, more preferably from 0.8 to 1.2, very preferably from 0.8 to 1.1.

Above a span $\Delta D$ of 1.4, the effect pigments obtained lack color purity. Effect pigments below a size distribution span of 0.7 are very costly and inconvenient to produce by the usual methods, and hence can no longer be produced economically.

The effect pigments of the invention may have any desired median particle size ($D_{50}$). The $D_{50}$ values of the effect pigments of the invention encompass a range from 3 to 350 µm. The effect pigments of the invention preferably have a $D_{50}$ value in a range of 3-15 µm or 10-35 µm or 25-45 µm or 30-65 µm or 40-140 µm or 135-250 µm.

The $D_{10}$ values of the effect pigments of the invention encompass preferably a range from 1 to 120 µm. Preferably the effect pigments of the invention have the combinations of $D_{90}$, $D_{50}$ and $D_{10}$ values as specified in Table 2. In the present case, the $D_{10}$, $D_{50}$, and $D_{90}$ values of Table 2 are combined only in such a way as to produce a span $\Delta D$ of 0.7-1.4. Combinations of $D_{10}$, $D_{50}$, and $D_{90}$ values that lead to a span which is not within the $\Delta D$ range of 0.7-1.4 are not inventive embodiments.

TABLE 2

Preferred combinations of ranges of $D_{90}$, $D_{50}$, and $D_{10}$ values

| $D_{90}$ (µm) | $D_{50}$ (µm) | $D_{10}$ (µm) |
|---|---|---|
| 8-25 | 3-15 | 1-5 |
| 20-45 | 10-35 | 5-25 |
| 40-70 | 25-45 | 10-30 |
| 70-110 | 30-65 | 20-45 |
| 120-180 | 40-140 | 25-65 |
| 400-490 | 135-250 | 75-110 |

It has surprisingly been found that the combinations of ranges of $D_{90}$, $D_{50}$ and $D_{10}$ values as specified in Table 2 produce effect pigments of extremely high color purity.

In this context it has surprisingly emerged that it is not the absolute size of the effect pigments that is critical but rather the proportion of the sizes to one another. It is critical that the span $\Delta D=(D_{90}-D_{10})/D_{50}$ is situated within a narrow range from 0.7 to 1.4. Within this range, for example, the $D_{50}$ values of the effect pigments may be 15, 20, 25, 30 µm or else 50, 80, 100, 150, 200, 250, 300 or 350 µm. It has been found that surprisingly, even in the case of a majority of relatively large effect pigments, effect pigments of color purity are obtained if the span $\Delta D$ is situated in a range from 0.7 to 1.4.

The average thickness of the artificial platelet-shaped substrates is 500 nm to 2000 nm and preferably 750 to 1500 nm.

The aspect ratio of the effect pigments of the invention, calculated from the quotient of particle diameter to thickness, is preferably 2-980, more preferably 5-950, and very preferably 10-920.

If substrates below an average thickness of 500 nm are coated with high-index metal oxides, then the substrate has a marked optical influence on the interference color of the system as a whole. The effect pigments obtained, consequently, no longer have the desired high color purity. Moreover, there is a marked decrease in the mechanical stability of these effect pigments with respect, for example, to shearing forces. Furthermore, the times taken to coat these thin substrates with, for example, high-index metal oxides or semi-transparent metals, owing to the high specific surface areas of these pigments, are very long, resulting in high production costs.

Above an average substrate layer thickness of 2000 nm, the effect pigments become too thick overall. This entails a poorer opacity and also a lower level of plane-parallel orientation within the application medium. The poorer orientation results in turn in a reduced luster.

In one preferred embodiment the standard deviation of the thickness of the artificial substrates is 15% to 100% and more preferably 20% to 70%.

The average thickness is determined on the basis of a cured paint film in which the effect pigments are oriented substantially plane-parallel to the substrate. For this purpose a transverse section of the cured paint film is examined under a scanning electron microscope (SEM), the thickness of 100 effect pigments being ascertained and statistically averaged.

Below a standard deviation of 15%, the effect pigments obtained exhibit color flop. Above a standard deviation of 100%, the collective of pigments as a whole contains so many relatively thick pigments that orientation is then poorer and hence luster is lost.

It has surprisingly been found that effect pigments whose artificial substrates have an average thickness of 500 to 2000 nm and also a span $\Delta D$ of 0.7 to 1.4 exhibit the desired extraordinary color purity at a constant angle of light incidence and angle of viewing.

The effect pigments are preferably pearlescent pigments or optically variable pigments.

The effect pigments of the invention may also be present here in a mixture with other effect pigments.

Effect pigments based on natural mica have been known for some considerable time. When using natural mica as a substrate, however, it is necessary to accept that its surface is not ideally smooth but instead has irregularities, such as steps, for example. These irregularities limit the quality of the resultant effect pigments, since they often lead to different colors within the same pigment platelet. This considerably reduces the color purity in particular. Furthermore, the foreign ion impurities that are present in natural mica may alter the perceived color of the effect pigments, with the consequence that a plurality of effect pigments originating from one production batch have differing colors or hues, thus giving the pigment mixture a low color purity.

These disadvantages of natural mica can be circumvented through the use of artificial substrates. Artificial substrates are substrates which do not occur as such in nature but instead must be synthesized. Suitable base substrates for the effect pigments of the invention are, for example, synthetic, nonmetallic, platelet-shaped substrates. The substrates are preferably substantially transparent, more preferably transparent.

One preferred variant of the invention uses as substrates glass platelets (i.e., glass flakes), platelets of synthetic mica, $SiO_2$ platelets, polymer platelets, platelet-shaped bismuth oxychloride and/or platelet-shaped aluminum oxides or mixtures thereof. For the effect pigments of the invention it is preferred to use substrates consisting of glass platelets or synthetic mica.

The effect pigments of the invention may be substrates provided with one or more optically active layers or coatings. An optically active layer or coating is a layer or coating at which incident light gives rise to perceptible color effects by virtue of physical effects such as reflection, interference, absorption, refraction, etc.

As optically active layers or coatings it is preferred to apply layers which comprise metal oxides, metal oxide hydrates, metal suboxides, metals, metal fluorides, metal nitrides, metal oxynitrides or mixtures thereof. In one preferred variant the optically active layers or coatings are composed of the aforementioned materials.

Unless indicated otherwise, the terms "layers" or "coatings" are used interchangeably for the purposes of this invention.

In one preferred variant of the invention a coating or two or more coatings may have a refractive index $n \geq 1.9$, and hence are high-index.

If the effect pigments of the invention have two or more layers, these layers, in relation to refractive index, are preferably arranged in alternation, so that a high-index layer having a refractive index of $n \geq 1.9$ is followed preferably by a low-index layer having a refractive index $n < 1.9$, or vice versa.

The coating in this case may either surround the entire substrate or be present only partially on the substrate. The metal oxide, metal oxide hydrate, metal suboxide, metal, metal fluoride, metal nitride or metal oxynitride layers, or layers with mixtures of the aforementioned compounds, may be low-index (refractive index<1.9) or high-index (refractive index $n \geq 1.9$).

In one preferred embodiment the substrate is or comprises a low-index platelet-shaped substrate and the coating has at least one high-index layer ($n \geq 1.9$). Substrate platelets used with preference are glass platelets, synthetic mica platelets and/or $SiO_2$ platelets.

Metal oxides and/or metal oxide hydrates used are preferably titanium oxide, titanium dioxide, titanium oxide hydrate, aluminum oxide, aluminum oxide hydrate, silicon oxide, silicon dioxide, iron oxide, iron hydroxide, tin oxide, chromium oxide, antimony oxide, cerium oxide or their mixed oxides.

In a further inventive embodiment of the invention the substrates are coated with metal layers. In this case it is preferred to apply semitransparent metal layers in order to provide effect pigments having interference colors in accordance with the Fabry-Perot effect.

Suitable metals for generating the semitransparent metal layers are, for example, aluminum, chromium, nickel, silver, gold, titanium, copper or their alloys.

The thickness of the semitransparent metal layers is situated preferably in a range from 4 to 40 nm and more preferably 5 to 30 nm.

As a metal fluoride, one variant applies magnesium fluoride as a coating. As metal nitrides or metal oxynitrides it is possible, for example, to use those of the metals titanium, zirconium and/or tantalum.

The substrate is coated preferably with metal oxide layers and/or metal oxide hydrate layers.

Examples of low-index layers include aluminum oxide, aluminum oxide hydrate, silicon oxide, silicon oxide hydrate and/or magnesium fluoride.

Examples of high-index layers used are titanium dioxide, titanium suboxides, iron oxide, iron hydroxide, tin oxide, zinc oxide, zirconium oxide, cerium oxide, cobalt oxide, chromium oxide, antimony oxide or their mixed oxides.

Different colors in the effect pigments of the invention can be set here through the choice of layer material and layer thickness, as shown for example by Table 1.

|  | Coating/layer thickness | Color |
| --- | --- | --- |
| Silver-white pearlescent pigments | $TiO_2$: 40-60 nm | silver |
| Interference pigments | $TiO_2$: 60-80 nm | yellow |
|  | $TiO_2$: 80-100 nm | red |
|  | $TiO_2$: 100-140 nm | blue |
|  | $TiO_2$: 120-160 nm | green |
|  | $TiO_2$: 280-320 nm | green (IIIrd order) |
| Color luster pigments | $Fe_2O_3$: 35-45 nm | bronze |
|  | $Fe_2O_3$: 45-55 nm | copper |
|  | $Fe_2O_3$: 55-65 nm | red |
|  | $Fe_2O_3$: 65-75 nm | red-violet |
|  | $Fe_2O_3$: 75-85 nm | red-green |
|  | $Fe_3O_4$ | black |
| Combination pigments | $TiO_2/Fe_2O_3$ | gold tones |
|  | $TiO_2/Cr_2O_3$ | green |
|  | $TiO_2$/Prussian Blue | dark blue |

Where the effect pigments of the invention have a coating with titanium dioxide, the titanium dioxide may be present in the rutile or anatase crystal polymorph. The best-quality and most stable pearlescent pigments are obtained when the titanium dioxide layer is in the rutile form. The rutile form can be obtained by, for example, applying a layer of $SnO_2$ to the substrate or the pigment before the titanium dioxide layer is applied. Applied to a layer of $SnO_2$, $TiO_2$ crystallizes in the rutile polymorph.

The thickness of the metal oxide, metal oxide hydrate, metal suboxide, metal, metal fluoride or metal nitride layers or of layers with a mixture of the aforementioned compounds is situated typically in a range of 30-350 nm, more preferably of 50-300 nm.

The metal oxide, metal oxide hydrate, metal suboxide, metal, metal fluoride and/or metal nitride layers may contain or comprise colorants such as Prussian Blue, ultramarine, carmine red, azopigments, phthalocyanines or FD & C dyes/lakes. These colorants may be present in the coating and/or applied to this coating and if necessary fixed thereon by adhesion promoters.

In order to provide better protection from weathering effects to the effect pigments of the invention they may additionally be coated with an outer protective layer. This layer comprises or is composed preferably of one or two metal oxide layers of the elements Si, Al or Ce. Particular preference is given here to a sequence in which first of all a cerium oxide layer is applied and is then followed by an SiO$_2$ layer, as described in WO 2006/021386 A1, hereby incorporated by reference.

The outer protective layer may also be organic-chemically modified on the surface. By way of example, one or more silanes may be applied to this outer protective layer. The silanes may be alkylsilanes having branched-chain or unbranched alkyl radicals of 1 to 24 C atoms, preferably 6 to 18 C atoms.

The silanes may alternatively be organofunctional silanes which allow chemical attachment to a plastic, a binder of a paint or of an ink, etc.

The organofunctional silanes which are used preferably as surface modifiers and which contain suitable functional groups are available commercially and are produced, for example, by Degussa, Rheinfelden, Germany and sold under the trade name "Dynasylan®". Other products can be acquired from OSi Specialties (Silquest® silanes) or from Wacker, examples being standard silanes and α silanes from the GENIOSIL® product group.

Examples thereof are 3-methacryloyloxypropyltrimethoxysilane (Dynasylan MEMO, Silquest A-174NT), vinyltri(m)ethoxysilane (Dynasylan VTMO or VTEO, Silquest A-151 or A-171), 3-mercaptopropyltri(m)ethoxysilane (Dynasylan MTMO or 3201; Silquest A-189), 3-glycidoxypropyltrimethoxysilane (Dynasylan GLYMO, Silquest A-187), tris-(3-trimethoxysilylpropyl)isocyanurate (Silquest Y-11597), gamma-mercaptopropyltrimethoxysilane (Silquest A-189), bis-(3-triethoxysilylpropyl) polysulfide (Silquest A-1289), bis-(3-triethoxysilyl) disulfide (Silquest A-1589), beta-(3,4-epoxycyclohexyl)ethyltrimethoxysilane (Silquest A-186), bis(triethoxysilyl)ethane (Silquest Y-9805), gamma-isocyanatopropyltrimethoxysilane (Silquest A-Link 35, GENIOSIL GF40), (methacryloyloxymethyl)tri(m)ethoxysilane (GENIOSIL XL 33, XL 36), (methacryloyloxymethyl)(m)ethyldimethoxysilane (GENIOSIL XL 32, XL 34), isocyanatomethyl)trimethoxysilane (GENIOSIL XL 43), (isocyanatomethyl)methyldimethoxysilane (GENIOSIL XL 42), (isocyanatomethyl)trimethoxysilane (GENIOSIL XL 43), 3-(triethoxysilyl)propylsuccinic anhydride (GENIOSIL GF 20), (methacryloyloxymethyl)methyldiethoxysilane, 2-acryloyloxyethylmethyldimethoxysilane, 2-methacryloyloxyethyltrimethoxysilane, 3-acryloyloxypropylmethyldimethoxysilane, 2-acryloyloxyethyltrimethoxysilane, 2-methacryloyloxyethyltriethoxysilane, 3-acryloyloxypropyltrimethoxysilane, 3-acryloyloxypropyltripropoxysilane, 3-methacryloyloxypropyltriethoxysilane, 3-methacryloyloxypropyltriacetoxysilane, 3-methacryloyloxypropymethyldimethoxysilane, vinyltrichlorosilane, vinyltrimethoxysilane (GENIOSIL XL 10), vinyltris(2-methoxyethoxy)silane (GENIOSIL GF 58) and vinyltriacetoxysilane.

It is also possible, however, to use other organofunctional silanes on the effect pigments of the invention.

Additionally it is possible to use aqueous prehydrolyzates which are obtainable commercially, for example, from Degussa. These include, among others, aqueous, alcohol-free aminosilane hydrolyzate (Dynasylan Hydrosil 1151), aqueous, alcohol-free, amino/alkyl-functional siloxane cooligomer (Dynasylan Hydrosil 2627), aqueous, alcohol-free diamino/alkyl-functional siloxane cooligomer (Dynasylan Hydrosil 2776), aqueous, alcohol-free amino/vinyl-functional siloxane cooligomer (Dynasylan Hydrosil 2907), aqueous, alcohol-free amino/alkyl-functional siloxane cooligomer (Dynasylan Hydrosil 2909), aqueous, alcohol-free epoxy-functional siloxane oligomer (Dynasylan Hydrosil 2926) or aqueous, alcohol-free amino/methacrylate-functional siloxane cooligomer (Dynasylan Hydrosil 2929), oligomeric diaminosilane system (Dynasylan 1146), vinyl/alkyl-functional siloxane cooligomer (Dynasylan 6598), vinyl- and methoxy-containing vinylsilane concentrate (oligomeric siloxane) (Dynasylan 6490) or oligomeric short-chain alkyl-functional silane (Dynasylan 9896).

In one preferred embodiment the organofunctional silane mixture, in addition to at least one silane without a functional binding group, comprises at least one amino-functional silane. The amino function is a functional group which is able to enter into one or more chemical interactions with the majority of groups present in binders. Said interactions may involve a covalent bond, such as with isocyanate or carboxylate functions of the binder, for example, or hydrogen bonds, such as with OH or COOR functions, or else ionic interactions. An amino function is therefore very suitable indeed for the purpose of the chemical attachment of the effect pigment to different kinds of binders.

The following compounds are taken preferably for this purpose:
Aminopropyltrimethoxysilane (Dynasylan AMMO; Silquest A-1110), aminopropyltriethoxysilane (Dynasylan AMEO) or N-(2-aminoethyl)-3-aminopropyltrimethoxysilane (Dynasylan DAMO, Silquest A-1120) or N-(2-aminoethyl)-3-aminopropyltriethoxysilane, triamino-functional trimethoxysilane (Silquest A-1130), bis(gamma-trimethoxysilylpropyl)amine (Silquest A-1170), N-ethyl-gamma-aminoisobutyltrimethoxysilane (Silquest A-Link 15), N-phenyl-gamma-aminopropyltrimethoxysilane (Silquest Y-9669), 4-amino-3,3-dimethylbutyltrimethoxysilane (Silquest Y-11637), N-cyclohexylaminomethylmethyldiethoxysilane (GENIOSIL XL 924), (N-cyclohexylaminomethyl)triethoxysilane (GENIOSIL XL 926), (N-phenylaminomethyl)trimethoxysilane (GENIOSIL XL 973), and mixtures thereof.

In one further-preferred embodiment the silane without a functional binding group is an alkyl silane. The alkyl silane preferably has the formula (A):

$$R_{(4-z)}Si(X)_z \qquad (A)$$

In this formula z is an integer from 1 to 3, R is a substituted or unsubstituted, unbranched or branched alkyl chain having 10 to 22 C atoms, and X is a halogen and/or alkoxy group. Preferred alkyl silanes have alkyl chains with at least 12 C atoms. R may also be connected cyclically to Si, in which case z is typically 2.

A silane of this kind has the effect of strong hydrophobicization of the pigment surface. This in turn leads to the pearlescent pigment thus coated having a tendency to float upward in the surface coating. In the case of platelet-shaped effect pigments, behavior of this kind is referred to as "leafing".

A silane mixture composed of at least one silane which possesses at least one functional group allowing attachment to the binder, and an alkyl silane which does not have an amino group and which is insoluble or virtually insoluble in water permits optimum performance properties on the part of the pearlescent pigments.

An organic-chemical surface modification of this kind means that the effect pigments exhibit excellent orientation in a paint or ink film, i.e., are oriented substantially plane-parallel with respect to the painted or coated substrate, and at the same time react chemically with the binder system of the paint or ink and hence are bound covalently in the paint or ink film. Paint or ink films of this kind exhibit enhanced mechanical and chemical resistance toward environmental effects, such as weather, etc.

When the effect pigments of the invention in an applicator drawdown (e.g., in a nitrocellulose varnish) are viewed in transmission under a light microscope, the effect pigments of the invention are seen to have a very uniform color. The individual pigments have largely the same color, preferably the same color.

The color imparted by effect pigments, such as pearlescent pigments, is as a result of interference phenomena. In the context of these phenomena, interference colors which are complementary to one another are mutually extinguished: thus, for example, a mixture of blue and yellow pearlescent pigments produces a silver or grey color. It is well known that mixtures of different-colored pearlescent pigments always produce a less pure hue with a lower luster, owing to the ever-present mutual extinction or attenuation of certain color fractions.

In order, therefore, to obtain effect pigments, preferably pearlescent pigments, having a high color purity, it is necessary for the hues of the individual pigments to be as uniform as possible. The purity of hue can be represented quantitatively by the following method in accordance with a statistical evaluation.

The starting point for determining the color purity of the effect pigments of the invention are digital color microscope images of applicator drawdowns. Applicator drawdown is carried out with a paint comprising 6% by weight effect pigments in a colorless nitrocellulose varnish. The percent by weight quantities here are based on the total weight of the paint. The paint is applied in a wet film thickness of 76 μm to a BYK-Gardner black-white drawdown chart (byko-chart 2853) and subsequently dried. Within these dried applicator drawdowns, the platelet-shaped effect pigments have a largely plane-parallel orientation. The microscope images are taken preferably using the Axioskop 2 microscope and the AxioCam digital camera from Zeiss, Germany. From the resulting digital images, the AxioVision 4.6 image-recording and image-processing software from Zeiss is then used to prepare color-neutral digital images with a 12-bit depth of color. When the applicator drawdowns are observed through the microscope, the irradiated light is incident vertically from above onto the applicator drawdown. In the applicator drawdown, in turn, the effect pigments have a largely plane-parallel orientation, and hence the incident light falls perpendicularly onto the pigment platelets. The viewing angle is in this case likewise perpendicular to the surface of the pigment platelets.

In order to obtain undistorted statistical data, around 20 individual micrographs were produced at randomly selected points on the black substrate of the applicator drawdowns. This constituted the imaging of more than 100 individual evaluable pigments.

Since the image-processing software is unable to recognize the pigments automatically, they are marked manually. In the marking of the individual pigment area fractions, care should be taken to ensure that there is no recording of pigment marginal regions or regions in which the pigments overlap, since in this case the perceived color of the individual pigment particles is immediately distorted by the overlap (see also FIG. 1).

For the areas thus marked, the image-processing software calculates the respective area means of the red, green, and blue fractions. For meaningful statistics, the color fractions of at least 100 evaluable pigment particles are determined from the various micrographs.

The image-processing software uses the sRGB color model. Conversion to the XYZ color space is accomplished via the well-known transformation matrix (II) (IEC 61966-2-1:1999).

$$\begin{pmatrix} X \\ Y \\ Z \end{pmatrix} = \begin{pmatrix} 0.4124 & 0.3576 & 0.1805 \\ 0.2126 & 0.7152 & 0.0722 \\ 0.0193 & 0.1192 & 0.9505 \end{pmatrix} \begin{pmatrix} R \\ G \\ B \end{pmatrix} \quad \text{(II)}$$

The resulting X, Y, and Z values are then converted into the customary CIE (1976) Lab values:

$$L^* = 116\, Y^* - 16 \quad \text{(III)}$$

$$a^* = 500\, (X^* - Y^*) \quad \text{(IV)}$$

$$b^* = 200\, (Y^* - Z^*) \quad \text{(V)}$$

$$X^* = \sqrt[3]{\frac{X}{X_n}} \quad \text{(VI)}$$

The calculation for Y* and Z* is made in a manner similar to that for the calculation of X*. The tristimulus values used were $X_n$=94.81, $Y_n$=100 and $Z_n$=107.34 for the D65 illuminant and the 10° standard observer.

This produces a distribution of measurement points in the a*-b* color space (see also FIG. 2): the distance of the measurement points from the origin of the a*,b* diagram determines the color saturation (chroma) C* of each individual measurement value.

The scattering is quantified by first calculating the common middle point ($\bar{a}$, $\bar{b}$) of the measurement values in the a*-b* color space in accordance with the formulae (VIIa; VIIb):

$$\bar{a} = \sum_i a_i \quad \text{(VIIa)}$$

$$\bar{b} = \sum_i b_i \quad \text{(VIIb)}$$

Subsequently, for each measurement point (a,b), its distance from the middle point ($\bar{a}$, $\bar{b}$) is determined as an absolute value ΔC* in the form of the root of the square of the difference in the values (VIII):

$$\Delta C^* = \sqrt{(a-\bar{a})^2 + (b-\bar{b})^2} \quad \text{(VIII)}$$

This gives a color difference distribution in the a*-b* color space. This distribution may likewise be represented in the form of a cumulative undersize distribution curve. The 90% quantile ($\Delta C^*_{90}$) of this color difference distribution is a suitable measure for characterizing the size of the color scattering (see FIG. 3). This figure marks the color difference ΔC* of the mean value below which 90% of the counted pigment particles are situated.

The effect pigments of the invention preferably have a 90% quantile of the color difference distribution $\Delta C^*_{90}$ of 0.2 to 8.0 and more preferably of 0.5 to 6.0; with further preference, of 0.6 to 5.0; with particular preference of 0.7 to 4.0, and with very particular preference of 0.7 to 3.0.

The inventors have not as yet found any scientifically meaningful explanation for this surprising effect. It is, however, thought that the pigment substrates which are largely the same in their size are coated substantially more uniformly with the coloring layers—as, for example, high-index metal oxides or semitransparent metals—than is the case for substrates having a greater span ΔD. As a result, coatings with a substantially more homogeneous layer thickness are formed on the substrates. Since the color is imparted as a result of interference phenomena, and in the case of the substrates used is determined critically by the layer thickness of the high-index coating, the more uniform layer thicknesses give rise to a purer hue or a greater color purity in the case of the effect pigments of the invention.

The present invention encompasses pearlescent pigments without color flop and also effect pigments with a high color flop in multilayer systems.

The critical factor, however, is that, at constant angle of incidence and angle of viewing in an applicator drawdown, with largely plane-parallel orientation of the platelet-shaped effect pigments of the invention, the hue observed is always largely the same in the sense of the present description. It is not necessary here for the angle of incidence and angle of viewing always to be perpendicular to the pigment platelets, although such a case is preferred.

The effect pigments of the invention are suitable more particularly for application in cosmetics, such as, for example, body powder, face powder, compact and loose powder, face makeup, powder cream, cream makeup, emulsion makeup, wax makeup, foundation, mousse makeup, blusher, eye makeup such as eye shadow, mascara, eyeliner, liquid eyeliner, eyebrow pencil, lip care stick, lipstick, lip gloss, lip liner, hair-styling compositions such as hairspray, hair mousse, hair gel, hair wax, hair mascara, permanent or semi-permanent hair colors, temporary hair colors, skin care compositions such as lotions, gels, and emulsions, and nail varnish compositions.

In order to obtain specific color effects in the cosmetic applications it is possible to use not only the effect pigments of the invention but also other colorants and/or conventional effect pigments or mixtures thereof, in variable proportions. Conventional effect pigments used may be, for example, commercial pearlescent pigments based on natural mica coated with high-index metal oxides (such as the Prestige® product group from Eckart, for example), BiOCl platelets, $TiO_2$ platelets, pearlescent pigments based on synthetic mica coated with high-index metal oxides or based on glass flakes or $Al_2O_3$, $SiO_2$ or $TiO_2$ platelets coated with high-index metal oxides. In addition it is also possible to add metallic effect pigments, such as the Visionaire® product group from Eckart, for example. The colorants may be selected from inorganic or organic pigments.

Preferred effect pigments for the purposes of the present invention possess a span ΔD of 0.7-1.4, preferably 0.7-1.3, more preferably 0.8-1.2, and very preferably 0.8-1.1, and a $D_{50}$ value of 3-350 μm. Their average thickness is 500-2000 nm; the standard deviation in the thickness is 15%-100%.

Further-preferred effect pigments for the purposes of the present invention possess a span ΔD of 0.8-1.2, a $D_{50}$ value of in each case preferably 3-15 μm, 10-35 μm, 25-45 μm, 30-65 μm, 40-140 μm or 135-250 μm. Their average thickness is 500-2000 nm, and the standard deviation in the thickness is 15%-100%.

Further-preferred effect pigments for the purposes of the present invention possess a span ΔD of 0.8-1.2 and an average thickness of 500-2000 nm, more preferably of 750-1500 nm. The standard deviation in the thickness is 15%-100%, and the effect pigments have a $D_{50}$ value of 3-350 μm.

Further-preferred effect pigments for the purposes of the present invention possess a span ΔD of 0.8-1.2 and a standard deviation in the thickness of 20%-70%. The average thickness of the effect pigments is 500-2000 nm, preferably 750-1500 nm. They have a $D_{50}$ value of 3-350 μm.

A process for producing the effect pigments of the invention comprises the following steps:
a) size-classifying the artificial substrates
b) coating the artificial substrates.

If the starting substrates are too large, it is possible optionally to carry out a comminuting step prior to the size-classifying.

The size classification may take place before or after the coating of the substrates. Advantageously, however, the substrate is first classified and then coated. The size classification is carried out and repeated as and where necessary, until the pearlescent pigments have the inventive particle size distribution.

A narrow span ΔD of the substrates can be achieved through suitable comminuting and/or classifying operations on the artificial substrates to be coated. The artificial substrates to be coated may be comminuted using, for example, a ball mill, jet or agitator ball mill, edge runner mill or dissolver. The span ΔD of the final fraction can be set by means of appropriate classification, such as by multiple wet sieving, for example. Further classification methods include centrifugation in cyclones or sedimentation from a dispersion.

The comminuting and classifying operations may take place in succession and as and where necessary may be combined with one another. For instance, a classifying operation may follow a comminuting operation, which is followed by a further comminuting operation on the fine fraction, and so on.

The object on which the invention is based is achieved, additionally, by the provision of a coating composition which comprises the effect pigments of any of claims 1 to 10. In one preferred variant the coating composition is selected from the group consisting of cosmetics, paint, printing ink, varnish, powder coating material, and electrocoat material.

The object on which the invention is based is further achieved by the provision of a plastic which comprises the effect pigments of any of claims 1 to 10.

In the text below, the invention is elucidated in more detail by a number of examples and figures, without being confined thereto.

EXAMPLES

Figure 1:
FIG. 1 shows a manually marked area fraction in a digital image of an effect pigment of the invention in a dried applicator drawdown.

The examples below are intended to elucidate the invention in more detail, but without restricting it thereto.

Example 1

A suspension of 200 g of glass flakes (average thickness: 1 μm, standard deviation of the thickness: around 40%) in DI water (around 3% by weight) (DI: deionized water: fully demineralized) is classified on a 100 µm sieve, and the sieve undersize is sieved in turn on a 63 µm sieve. This sieving procedure is repeated twice with the residue obtained on the 63 µm sieve, to give a glass flake fraction whose particle size distribution (MALVERN Mastersizer MS 2000) is as follows: $D_{10}$=50 µm, $D_{50}$=82 µm, $D_{90}$=132 µm, Span $\Delta D$=1.00.

Example 2

200 g of glass flakes from example 1 are suspended in 2000 ml of deionized water and the suspension is heated to 80° C. with turbulent stirring. The pH of the suspension is adjusted to 1.9 using dilute HCl and then a first layer of "SnO$_2$" is precipitated onto the glass flakes. This layer is formed by addition of a solution consisting of 3 g of SnCl$_4$×5H$_2$O (in 10 ml of concentrated HCl plus 50 ml of deionized water), with simultaneous metering of 10% NaOH in order to keep the pH constant, over a period of 1 hour. In order to complete the precipitation, the suspension is stirred for a further 15 minutes. Thereafter the pH is lowered to 1.6 using dilute HCl, and a solution of 200 ml of TiCl$_4$ (400 g TiCl$_4$/l deionized water) is then metered into this suspension. The pH is kept at a constant 1.6 by counter-addition of 10% NaOH. This is followed by stirring for 15 minutes more and by filtration, the filter cake being rinsed with deionized water. The filter cake is then subjected to initial drying at 100° C. and to calcining at 750° C. for 30 minutes. A highly lustrous effect pigment is obtained which shows a red interference color. Microscopic investigation of the coated pigments shows extraordinary consistency in the color of the pigments.

Example 3

200 g of glass flakes from example 1 are coated by the method of example 2 with TiO$_2$, but with metered addition of only 167 ml of TiCl$_4$. The product after calcining is a highly lustrous effect pigment having a golden interference color. Microscopic investigation, in the same way as in example 2, shows an extraordinary consistency in color of the pigments.

Comparative Example 4

Commercially available golden pearlescent "Reflecks Dimension Sparkling Gold" pigments from BASF Catalysts.

Comparative Example 5

Commercially available golden pearlescent "RonaStar Golden Sparks" pigments from Merck.

TABLE 3

Characteristic size distribution values for some inventive and comparative examples:

| Pigment | $D_{10}$ | $D_{50}$ | $D_{90}$ | Span $\Delta D$ |
|---|---|---|---|---|
| Ronastar Golden Sparks (comparative example 4) | 34.0 | 78.4 | 148.7 | 1.46 |
| Reflecks Dimension Sparkling Gold (comparative example 5) | 35.6 | 84.3 | 175.9 | 1.66 |
| Example 3 | 49.8 | 81.5 | 130.7 | 0.99 |

Below, the inventive effect pigments of example 3, with a narrow span and high color purity, were compared in a detailed analysis with the commercially available pearlescent pigments of the comparative examples. All of the pearlescent pigments in the form of an applicator drawdown have a golden interference color which is perceptible visually to the observer.

The starting point for the determination of the color purity of the inventive effect pigments were digital color microscope images of dried applicator drawdowns (produced with a paint containing 6% by weight pigments in nitrocellulose varnish (% by weight figure is based on the total weight of the paint) and knife-coated in a wet film thickness of 76 µm onto a BYK-Gardner black-white drawdown chart (bykochart 2853), and subsequently dried at room temperature). These images were recorded using the Axioskop 2 microscope and the AxioCam digital camera from Zeiss. This equipment allowed the preparation, with the aid of the AxioVision 4.6 image-recording and image-processing software, of color-neutral digital images with a 12-bit depth of color.

In order to obtain distortion-free statistical data, around 20 individual micrographs were taken at randomly selected locations on the applicator drawdowns. Over 100 individual evaluable pigments were imaged in this procedure.

Figure 2:
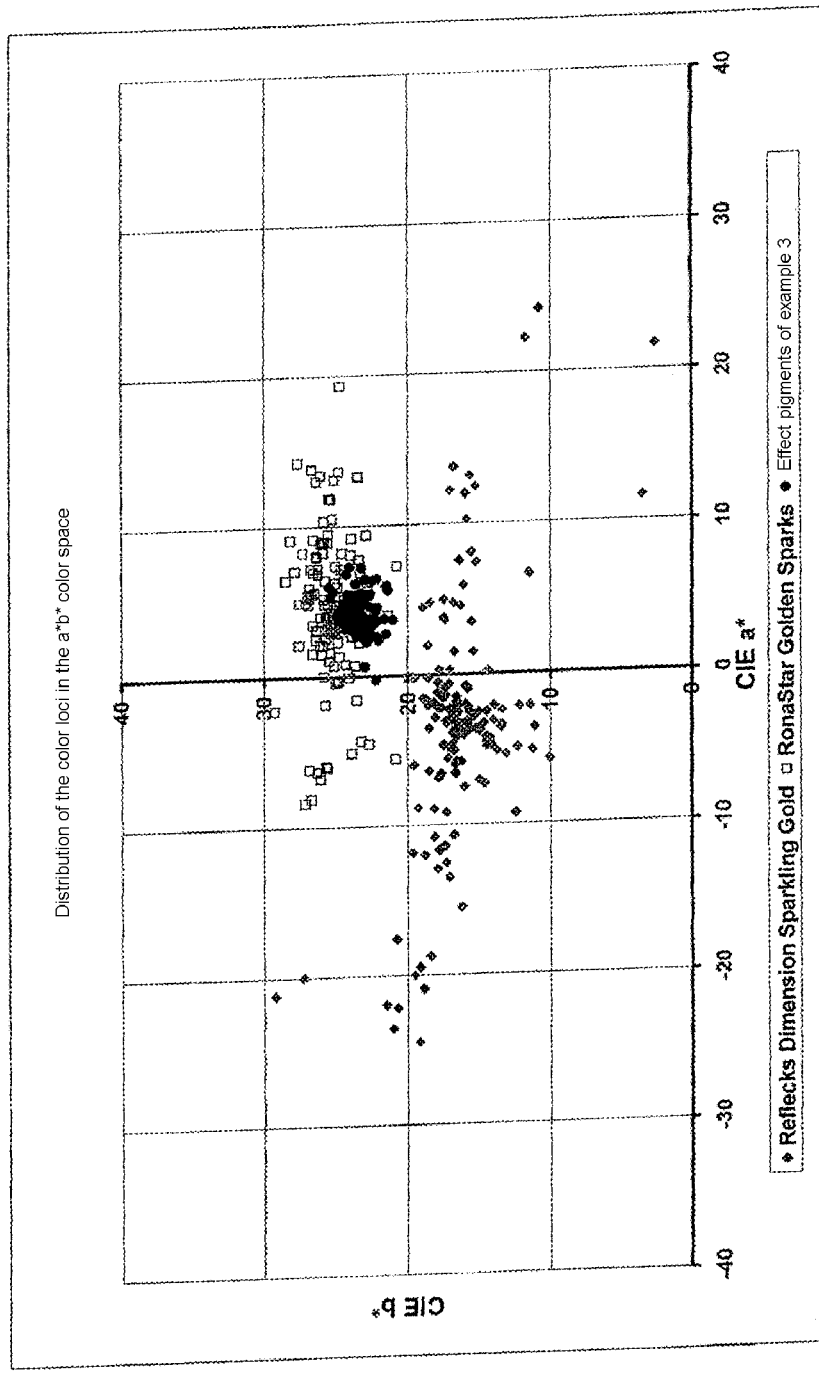
FIG. 2 shows the distribution of the color loci, calculated from the digital images of the manually marked effect pigments, in an a*b* color space.
Figure 3:
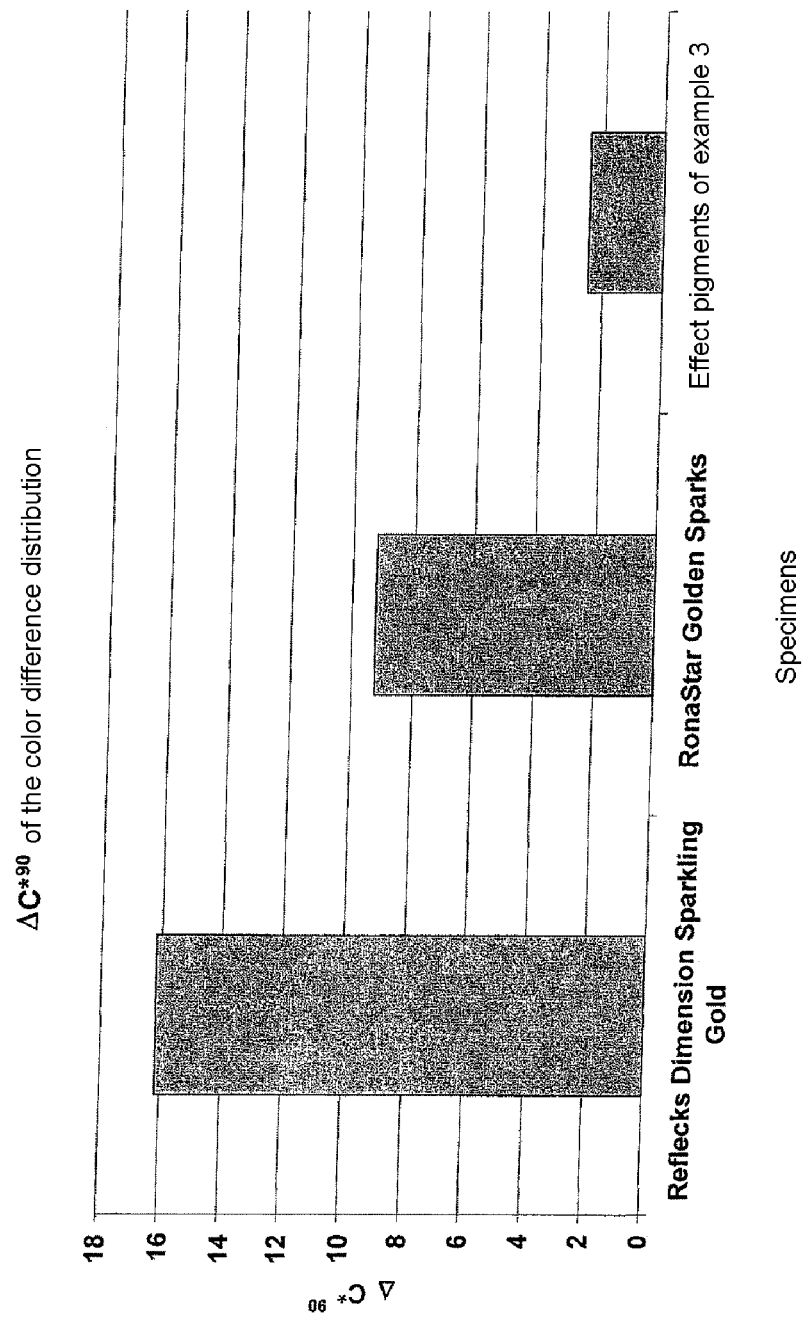
FIG. 3 shows the 90% quantile $\Delta C^*_{90}$ of the color difference distribution.

In FIG. 2 the color loci of the individual measurements of the three samples are plotted in the a*,b* diagram. It is clearly evident that the inventive effect pigments, in contrast to the commercially available products, have the lowest scattering in the a*-b* color space, i.e., have the purest color. The color values are situated closely together in the red-yellow quadrant of the a*-b* color space. The greatest scattering, i.e., the pigments colored with the least uniformity, is observed for the pigments of comparative example 4. This is also apparent even with the naked eye from the applicator drawdowns. A somewhat narrower scattering, but nevertheless a distribution over the green-yellow and red-yellow quadrants of the a*-b* color space, is present in the case of the Merck Ronastar pigments (Merck, Darmstadt, Germany).

TABLE 4

$\Delta C^*_{90}$ quantile

| Pigment | $\Delta C^*_{90}$ quantile |
|---|---|
| Ronastar Golden Sparks (comparative example 4) | 9.2 |
| Reflecks Dimension Sparkling Gold (comparative example 5) | 16.2 |
| Example 3 | 2.5 |

The 90% quantile of the color difference distribution is the lowest for the inventive effect pigments of inventive example 3, whereas the commercially available comparison products exhibit significantly higher values.

Example 6

200 g of glass flakes from example 1 are suspended in 2000 ml of deionized water and the suspension is heated to 80° C. with turbulent stirring. The pH of the suspension is adjusted to 1.9 using dilute HCl and then a first layer of "SnO$_2$" is precipitated onto the glass flakes. This layer is formed by addition of a solution consisting of 3 g of SnCl$_4$×5H$_2$O (in 10 ml of concentrated HCl plus 50 ml of deionized water), with simultaneous metering of 10% NaOH in order to keep the pH constant, over a period of 1 hour. In order to complete the precipitation, the suspension is stirred for a further 15 minutes. Thereafter the pH is lowered to 1.6 using dilute HCl, and a solution of 185 ml of $TiCl_4$ (400 g $TiCl_4$/l deionized water) is then metered into this suspension. The pH is kept at a constant 1.6 by counter-addition of 10% NaOH. Thereafter the pH is raised to 7.5 using 5% NaOH, and stirring takes place for 15 minutes. A waterglass solution (207 g of waterglass solution, 27% $SiO_2$, mixed with 207 g of deionized water) is then introduced slowly into the suspension, and the pH is kept constant at 7.5. This is followed by stirring for 20 minutes more, and the pH is lowered again to 1.9. Then a second layer of "$SnO_2$" is deposited on the $SiO_2$ surface. This layer is formed by addition of a solution consisting of 3 g of $SnCl_4 \times 5H_2O$ (in 10 ml of concentrated HCl plus 50 ml of deionized water), with simultaneous metered addition of a 10% NaOH, in order to keep the pH constant, over a period of 1 hour. In order to complete the precipitation, the suspension is stirred for a further 15 minutes. After that the pH is lowered to 1.6 using dilute HCl, and a solution of 189 ml of $TiCl_4$ (400 g $TiCl_4$/l deionized water) is then metered into the suspension. In the course of this procedure, the pH is kept constant at 1.6 by counter-addition of 10% NaOH. This is followed by stirring for 15 minutes more and by filtration, the filter cake being rinsed with deionized water. The filter cake is then subjected to initial drying at 100° C. and to calcining at 750° C. for 30 minutes. An extremely highly lustrous effect pigment is obtained which exhibits a color flop, with a change from a green interference color for steep viewing angles into a blue interference color at a shallow viewing angle.

Presented below are cosmetic applications with the inventive effect pigments:

Example 7: Body Powder

| INCI Name | Product Name | % W/W | Supplier |
|---|---|---|---|
| A | | 100.00 | |
| Mica | Silk Mica | ad 100 | www.vwr.com |
| Talc | Talc Powder | 18.00 | www.riedeldehaen.com |
| Boron Nitride | Softouch CCS 102 | 5.00 | www.advceramics.com |
| Nylon 12 | Orgasol 2002 D/Nat | 8.00 | www.atofinachemicals.com |
| Magnesium Stearate | Magnesium Stearate | 6.00 | www.sigmaaldrich.com |
| Methylparaben, Propylparaben | Rokonsal SSH-1 | 0.30 | www.biochema.com |
| Mica (and) Iron Oxides | Prestige ® Soft Bronze | 9.00 | www.eckart.net |
| Effect pigment of example 2/3 | — | 0.10-15.00 | |
| Mica (and) Titanium Dioxide | Prestige ® Magic Orange | 9.00 | www.eckart.net |
| B | | | |
| Tridecyl Stearate (and) Tridecyl Trimellitate (and) Dipentaerythrityl Hexacaprylate/Hexacaprate | Lipovol MOS-130 | 2.00 | www.lipochemicals.com |

Preparation:
1. Mix components of phase A
2. Add phase B to phase A
3. Mix and dispense into suitable container Example 8: Cream Eye Shadow

| INCI Name | Product Name | % W/W | Supplier |
|---|---|---|---|
| A | | 100.00 | |
| Castor Oil | Castor Oil | ad 100 | www.riedeldehaen.com |
| Octyl Palmitate | Liponate EHP | 6.00 | www.lipochemicals.com |
| *Cocos Nucifera* (Coconut) Oil | Lipovol C-78 | 7.00 | www.lipochemicals.com |
| Bees Wax | Ewacera 12 | 6.00 | www.wagnerlanolin.com |
| Isopropyl Lanolate | Ewalan IP | 5.00 | www.wagnerlanolin.com |
| *Persea Gratissima* (Avocado) Oil and Hydrogenated Avocado Oil | Avocado Butter | 7.00 | www.impag.de |
| Magnesium Stearate | Magnesium Stearate | 3.00 | www.sigmaaldrich.com |
| Bis-Hydroxyethoxypropyl Dimethicone | Dow Corning 5562 Carbinol Fluid | 7.00 | www.dowcorning.com |
| Dimethicone/Vinyl Dimethicone Crosspolymer and Silica | Dow Corning 9701 Cosmetic Powder | 5.00 | www.dowcorning.com |
| Phenoxyethanol (and) Methylparaben (and) Ethylparaben (and) Butylparaben | Uniphen P-23 | 0.30 | www.induchem.com |
| B | | | |
| Mica (and) Iron Oxides | Prestige ® Soft Breeze | 21.00 | www.eckart.net |
| Effect pigment of example 2/3 | — | 0.10-20.00 | |

Preparation:
1. Mix phase A and heat to 85° C.
2. Mix phase B
3. Add phase B to phase A with stirring
4. In suitable container, allow to cool to room temperature

Example 9: Foundation

| INCI Name | Product Name | % W/W | Supplier |
|---|---|---|---|
| A | | 100.00 | |
| Hydrogenated Polydecene | Ritadecene 20 | 9.00 | www.ritacorp.com |
| Caprylic/Capric Triglyceride | Liponate GC-K | 5.00 | www.lipochemicals.com |
| *Prunus Amygdalus Dulcis* (Sweet Almond) Oil | Sweet Almond Oil | 4.00 | www.jandekker.com |
| Caprylyl Trimethicone | SilCare Silicone 31M50 | 4.00 | www.clariant.com |
| Caprylyl Methicone | SilCare Silicone 41M16 | 3.00 | www.clariant.com |
| Steareth-2 | Volpo S2 | 1.60 | www.croda.com |
| Steareth-20 | Sympatens AS/200 G | 2.40 | www.kolb.ch |
| B | | | |
| Talc | Talc Powder | 4.50 | www.vwr.com |
| Mica (and) Iron Oxides | Prestige ® Soft Beige | 4.00 | www.eckart.net |
| Mica (and) Titanium Dioxide | Prestige ® Soft Silver | 1.00 | www.eckart.net |
| Effect pigment of example 2/3 | — | 0.05-1.00 | |
| C | | | |
| Glycerin | Pricerine 9090 | 5.00 | www.brenntag.com |
| Water | Aqua | ad 100 | |
| Ammonium Acryloyldimehtyltaurate/VP Copolymer | Aristoflex AVC | 0.40 | www.simon-undwerner.com |
| D | | | |
| Propylene Glycol (and) Diazolidinyl Urea (and) Methylparaben (and) Propylparaben | Nipaguard PDU | 0.40 | www.simort-undwerner.com |

Preparation:
1. Heat phase A to 70° C. with stirring
2. Add components of phase B to phase A
3. Mix phase C until Aristoflex is dissolved
4. Heat the mixture to 70° C.
5. Add phase C to phase AB
6. Allow to cool to 40° C., and add phase D

Example 10: Lip Gloss

| INCI Name | Product Name | % W/W | Supplier |
|---|---|---|---|
| A | | 100.00 | |
| Hydrogenated Polyisobutene (and) Ethylene/Propylene/Styrene Copolymer (and) Butylene/Ethylene/Styrene Copolymer | Versagel ME 750 | ad 100 | www.penreco.com |
| *Simmondsia Chinensis* (Jojoba) Seed Oil | Jojoba Oil - Natural/Golden | 2.00 | www.biochemica.com |
| Caprylyl Trimethicone | Silcare Silicone 31M50 | 7.00 | www.clariant.com |
| Stearyl Dimethicone | Silcare Silicone 41M85 | 3.20 | www.clariant.com |
| Hydrogenated Polydecene | Nexbase 2002 | 4.00 | www.jandekker.com |
| Isopropyl Myristate | Isopropyl Myristate | 4.50 | www.vwr.com |
| B | | | |
| Effect pigment of example 2/3 | — | 0.01-2.00 | |
| Propylparaben | Propyl-4-hydroxybenzoate | 0.20 | www.sigmaaldrich.com |

Preparation:
1. Heat phase A to 85° C.
2. Add phase B to phase A, mix and then dispense into suitable container

Example 11: Lip Liner

| INCI Name | Product Name | % W/W | Supplier |
|---|---|---|---|
| A | | 100.00 | |
| Hydrogenated Coco-Glycerides | Softisan 100 | 12.35 | www.sasolwax.com |
| Candelilla Wax | Ewacera 42 | 14.00 | www.wagnerlanolin.de |
| Magnesium Stearate | Magnesium Stearate | 6.00 | www.sigmaaldrich.com |
| Stearic Acid | Kortacid 1895 | 8.50 | www.akzonobel.com |
| Hydrogenated Coconut Oil | Lipex 401 | 8.00 | www.karlshamns.com |
| Cetyl Palmitate | Walrath synthetic | 7.00 | www.kahlwax.de |
| Caprylic/Capric Triglyceride | Liponate GC-K | 3.50 | www.lipochemicals.com |
| Soybean Glycerides (and) *Butyrospermum Parkii* | Lipex L'sens | ad 100 | www.karlshamns.com |
| Tocopheryl Acetate | D,L-Alpha-Tocopherol acetate | 0.25 | www.dsm.com |
| Methylparaben; Propylparaben | Rokonsal SSH-1 | 0.30 | www.biochema.com |
| B | | | |
| Mica (and) Titanium Dioxide (and) Ferric Ferrocyanide | Prestige ® Sapphire | 7.50 | www.eckart.net |
| Mica (and) Iron Oxides | Prestige ® Copper | 7.50 | www.eckart.net |
| Mica (and) Titanium Dioxide | Prestige ® Soft Silver | 5.00 | www.eckart.net |
| Effect pigment of example 2/3 | — | 0.10-10.00 | |

Preparation:
1. Heat phase A to 85° C.
2. Add phase B to phase A, mix and then dispense into suitable container

Example 12: Lip-Stick

| INCI Name | Product Name | % W/W | Supplier |
|---|---|---|---|
| A | | 100.00 | |
| Carnauba Wax | Ewacera 34 | 4.50 | www.wagnerlanolin.de |
| Bees Wax | Ewacera 12 | 3.50 | www.wagnerlanolin.de |
| Candelilla Wax | Ewacera 42 | 4.00 | www.wagnerlanolin.de |
| Microcrystalline Wax | Parcera MW | 7.20 | www.paramelt.com |
| Cetyl Palmitate | Walrath synthetic | 2.00 | www.kahlwax.de |
| Hydrogenated Coco-Glycerides | Softisan 100 | 5.00 | www.sasolwax.com |
| Petrolatum | Penreco Blond | 5.80 | www.penreco.com |
| Cetearyl Octanoate | Luvitol EHO | 10.70 | www.basf.com |
| Tocopheryl Acetate | D,L-Alpha-Tocopherol acetate | 0.50 | www.dsm.com |
| Castor Oil | Castor Oil | ad 100 | www.riedeldehaen.com |
| B | | | |
| Mica (and) Iron Oxide | Prestige ® Fire-red | 16.00 | www.eckart.net |
| Effect pigment of example 2/3 | — | 0.01-5.00 | |
| Methylparaben, Propylparaben | Rokonsal SSH-1 | 0.20 | www.biochema.com |

Preparation:
1. Heat phase A to 85° C.
2. Add phase B to phase A; after mixing at 75° C. dispense into suitable container

Example 13: Liquid Eyeliner

| INCI Name | Product Name | % W/W | Supplier |
|---|---|---|---|
| A | | 100.00 | |
| Water | Aqua | ad 100 | |
| Water/carbon black dispersion | MBD 201 | 3.00 | www.geotech.nl |
| Acrylates Copolymer | Covacryl E14 | 10.00 | www.lcw.fr |
| Magnesium Aluminium Silicate | Veegum HV | 1.00 | www.cherbsloeh.de |

| INCI Name | Product Name | % W/W | Supplier |
|---|---|---|---|
| B | | | |
| Propylene Glycol | 1,2 Propanediol | 3.00 | www.vwr.com |
| Triethanolamine | Triethanolamine | 1.40 | www.vwr.com |
| C | | | |
| Xanthan Gum | Keltrol T | 0.30 | www.cpkelco.com |
| D | | | |
| Effect pigment of example 2/3 | — | 0.10-5.00 | |
| Mica | Silk Mica | 2.00 | www.vwr.com |
| E | | | |
| Stearic Acid | Kortacid 1895 | 2.80 | www.akzonobel.de |
| Glyceryl Stearate | Aldo MS K FG | 0.80 | www.lonza.com |
| Oleyl Alcohol | HD-Ocenol 90/95 V | 0.50 | www.biesterfeld.com |
| Phenoxyethanol (and) Methylparaben (and) Ethylparaben (and) Butylparaben | Uniphen P-23 | 0.50 | www.induchem.com |
| F | | | |
| Dimethicone (and) Trisiloxane | Dow Corning 2-1184 Fluid | 5.00 | www.dowchemicals.com |

Preparation:
1. Disperse Veegum into phase A
2. Stir for 15 minutes
3. Add phase B to phase A
4. Add phase C to phase AB
5. Stir for 10 minutes
6. Add phase D to phase ABC and heat to 75° C.
7. Heat phase E to 75° C.
8. Add phase E to phase ABCD
9. Allow to cool to 60° C., and add phase F Example 14: Mascara

| INCI Name | Product Name | % W/W | Supplier |
|---|---|---|---|
| A | | 100.00 | |
| Water | Aqua | ad 100 | |
| Propylene Glycol | 1,2-Propanediol | 1.50 | www.vwr.com |
| Effect pigment of example 2/3 | — | 0.10-8.00 | |
| Cosmetic Black Oxide | C 33-134 Cosmetic Black Oxide | 7.00 | www.sunchemical.com |
| Caprylic/Capric Triglyceride | Liponate GC-K | 2.00 | www.lipochemicals.com |
| Hydroxyethylcellulose | Cellosize HEC QP-52000H | 0.30 | www.dow.com |
| Magnesium Aluminum Silicate | Veegum HV | 1.80 | www.rtvanderbilt.com |
| B | | | |
| Carnauba Wax | Ewacara 34 | 3.00 | www.wagnerlanolin.de |
| Bees Wax | Ewacara 12 | 3.00 | www.wagnerlanolin.de |
| Glyceryl Stearate | Imwitor 960 K | 3.00 | www.sasolwax.com |
| Cetyl Alcohol | Cetyl Alcohol | 3.80 | www.vwr.com |
| Polysorbate 60 | Tween 60 V | 1.00 | www.uniqema.com |
| PVP/VA Copolymer | Luviskol VA 64 | 2.00 | www.basf.com |
| C | | | |
| Water | Aqua | 4.00 | |
| BHT | Tenox BHT Kosher | 0.10 | www.eastman.com |
| Methylparaben | Methyl-4-hydroxybenzoate | 0.20 | www.sigmaaldrich.com |

Preparation:
1. Heat phase A to 85° C. with stirring
2. Heat phase B to 85° C.
3. Add phase B to phase A
4. Allow to cool to 55° C. with stirring
5. Add phase C, mix, dispense into suitable container Example 15: Mousse

| INCI Name | Product Name | % W/W | Designated use |
|---|---|---|---|
| A | | 100.00 | |
| Cyclopentasiloxane | Dow Corning 245 Fluid | 8.60 | www.dowcorning.com |

-continued

| INCI Name | Product Name | % W/W | Designated use |
|---|---|---|---|
| Hydrogenated Polyisobutene | MC 30 | 4.00 | www.sophim.com |
| Dimethicone (and) Dimethicone Crosspolymer | Dow Corning 9041 Silicone Elastomer Blend | ad 100 | www.dowcorning.com |
| Squalane | Squalane | 5.74 | www.impag.de |
| Isononyl Isononanoate | Dermol 99 | 10.16 | www.alzointernational.com |
| Hydrogenated Jojoba Oil | Jojoba Butter LM | 2.15 | www.desertwhale.com |
| Hydrogenated Jojaba Oil | Jojoba Butter HM | 1.00 | www.desertwhale.com |
| C30-45 Alkyl Methicone (and) C30-45 Olefin | Dow Corning AMS-C30 Cosmetic Wax | 1.15 | www.dowcorning.com |
| Stearyl Dimethicone | Dow Corning 2503 Cosmetic Wax | 0.47 | www.dowcorning.com |
| Cyclopentasiloxane (and) Polypropylsilsesquioxane | Dow Corning 670 Fluid | 5.00 | www.dowcorning.com |
| B | | | |
| Dimethicone/Vinyl Dimethicone Crosspolymer | Dow Corning 9506 Powder | 16.02 | www.dowcorning.com |
| Silica Dimethyl Silylate | Covasilic 15 | 0.17 | www.lcw.fr |
| Talc | Talc Powder | 5.00 | www.riedeldehaen.com |
| Mica (and) Titanium Dioxide (and) Iron Oxides | Prestige ® Soft Beige | 5.00 | www.eckart.net |
| Effect pigment of example 2/3 | — | 0.05-10.00 | |
| C | | | |
| Propylene Glycol, Diazolidinyl Urea, Methylparaben, Propylparaben | Germaben II | 0.40 | www.ispcorp.com |

Preparation:
1. Mix phase A, heat until all is melted
2. Premix phase B with speed mixer (2400 rpm, 1 min)
3. Add half of melted phase A to phase B, mix in speed mixer (2400 rpm, 30 s)
4. Add remainder of phase A to phase B and mix in speed mixer (2400 rpm, 30 s)
5. Add phase C, mix in speed mixer (2400 rpm, 30 s), allow to cool to room temperature Example 16: Nail Polish

| INCI Name | Product Name | % W/W | Supplier |
|---|---|---|---|
| A | | 100.00 | |
| Effect pigment of example 2/3 | — | 0.05-3.50 | |
| B | | | |
| International Lacquers Nailpolish & Care Base 359 | Butyl acetate (and) Ethyl acetate (and) Nitrocellulose (and) Isopropyl Alcohol | 100 ad | www.internationallacquers.lu |

Preparation:
1. Mix phases A and B with stirring
2. Dispense into suitable container Example 17: Pressed Eye Shadow

| INCI Name | Product Name | % W/W | Supplier |
|---|---|---|---|
| A | | 100.00 | |
| Mica | Silk Mica | 17.00 | www.vwr.com |
| Boron Nitride | Softouch CCS 1002 | 2.50 | www.advceramicscos.com |
| Talc | Talc Powder | ad 100 | www.riedeldehaen.com |
| Zinc Stearate | Kemilub EZ-V | 7.00 | www.undesa.com |
| Mica (and) Iron Oxides | Prestige ® Bright Fire-red | 39.00 | www.eckart.net |
| Effect pigment of example 2/3 | — | 0.05-8.00 | |

| INCI Name | Product Name | % W/W | Supplier |
|---|---|---|---|
| B | | | |
| Dimethicone | Dow Corning ® 200 Fluid 5 cst | 5.00 | www.dowcorning.com |
| Cyclomethicone (and) Dimethicone Crosspolymer | Dow Corning ® 9040 Elastomer | 5.00 | www.dowcorning.com |

Preparation:
1. Mix phase A
2. Add phase B and homogenize
3. Press eyeshadow at 150 bar for 30 minutes

Example 18: Pressed Powder

| INCI Name | Product Name | % W/W | Supplier |
|---|---|---|---|
| A | | 100.00 | |
| Talc | Talc Powder | ad 100 | www.riedeldehaen.com |
| Zinc Stearate | Kemilub EZ-V | 5.00 | www.undesa.com |
| Methylparaban, Propylparaben | Rokonsal SSH-1 | 0.30 | www.biochema.com |
| Polyethylene | Asensa CL 111 | 20.50 | www.honeywell.com |
| Silica | Syloblanc 34 | 1.50 | www.gracedavision.com |
| Mica (and) Titanium Dioxide | Prestige ® Soft Silver | 6.00 | www.eckart.net |
| Mica (and) Titanium Dioxide (and) Iron Oxides | Prestige ® Soft Beige | 11.00 | www.eckart.net |
| Effect pigment of example 2/3 | — | 0.05-8.00 | |
| B | | | |
| Octyl Palmitate | Liponate EHP | 3.00 | www.lipochemicals.com |

Preparation:
1. Mix phase A
2. Add phase B and homogenize
3. Press eyeshadow at 150 bar for 30 minutes

Example 19: Shower Gel

| INCI Name | Product Name | % W/W | Supplier |
|---|---|---|---|
| A | | 100.00 | |
| Effect pigment of example 2/3 | — | 0.01-1.00 | |
| Water | Aqua | ad 100 | |
| Blue 1 (0.5% aqueous solution) | FD&C Blue No. 1 | 0.10 | www.sunchemicals.com |
| Acrylates/C10-30 Alkyl Acrylate Crosspolymer | Carbopol ETD 2020 | 1.00 | www.noveon.com |
| Propylene Glycol | 1,2-Propanediol | 1.00 | www.vwr.com |
| B | | | |
| TEA- Lauryl Sulfate | Texapon T 42 | 22.00 | www.cognis.com |
| Cocamide Dea | Rewomid DC 212 S | 3.00 | www.degussa.com |
| Cocamidopropyl Betaine | Tego Betain F 50 | 4.00 | www.cognis.com |
| Disodium EDTA | Edeta BD | 0.05 | www.basf.com |
| C | | | |
| Triethanolamine | Triethanolamine | 0.30 | www.vwr.com |
| Phenoxyethanol, Ethylhexylglycerin | Euxyl PE 9010 | 0.60 | www.schuelke-mayr.com |

Preparation:
1. Disperse Carbopol in phase A
2. Heat to 65° C.
3. Gradually add ingredients from phase B
4. Allow to cool with stirring, at 40-45° C. add phase C Example 20: Styling Soft Wax

| INCI Name | Product Name | % W/W | Supplier |
|---|---|---|---|
| A | | 100.00 | |
| Effect pigment of example 2/3 | — | 0.01-2.00 | |
| Water | Aqua | ad 100 | |
| Propylene Glycol | 1,2 Propanediol | 2.00 | www.vwr.com |
| Glycerin | Pricerine 9090 | 7.00 | www.uniqema.ccm |
| Methoxy PEG/PPG-7/3 Aminopropyl Dimethicone | Abil Soft AF 100 | 0.50 | www.degussa.com |
| B | | | |
| Isosteareth-20 | Procol IS-20 | 14.50 | www.protameen.com |
| Laureth-4 | Genapol LA 040 | 10.00 | www.clariant.com |
| Paraffinum Liquidium | Paraffinum Liquidium | 6.00 | www.heess.de |
| C12-15 Alkyl Benzoate | Sympatens- LBZ | 8.00 | www.kolb.ch |
| C | | | |
| Phenoxyethanol (and) Methylparaben (and) Butylparaben (and) Ethylparaben (and) Propylparaben (and) Isobutylparaben | Phenonip | 0.40 | www.clariant.com |
| Fragrance | Cool Floral OA D | 0.10 | www.bell-europe.com |

Preparation:
1. Heat phases A and B separately to 90° C.
2. Add phase B to phase A with stirring
3. Allow to cool to 55° C.
4. Add phase C and dispense into a suitable container Example 21: Sun Protection Cream

| INCI Name | Product Name | % W/W | Supplier |
|---|---|---|---|
| A | | 100.00 | |
| Sorbitan Stearate (and) Methyl Glucose Sesquistearte | Sympatens-O/2500 G | 5.00 | www.kolb.ch |
| Stearic Acid | Kortacid 1895 | 4.00 | www.akzonobel.com |
| Octyldodecanol | Eutanol G | 9.00 | www.cognis.com |
| Caprylic/Capric Triglyceride | Liponate GC-K | 10.00 | www.lipochemicals.com |
| Cetearyl Alcohol | Lanette O | 2.00 | www.cognis.com |
| *Macadamia ternifolia* Seed Oil | Macadamia Nut Oil | 3.20 | www.jandekker.com |
| Octyl Methoxycinnamate | Parsol MCX | 1.00 | www.dsm.com |
| Butyl Methoxydibenzoylmethane | Parsol 1789 | 5.00 | www.roche.com |
| B | | | |
| Effect pigment of example 2/3 | — | 0.05-3.00 | |
| Water | Aqua | ad 100 | |
| Glycerin | Pricerine 9090 | 3.20 | www.uniqema.com |
| C | | | |
| Phenoxyethanol (and) Methylparaben (and) Ethylparaben (and) Butylparaben | Uniphen P-23 | 0.40 | www.induchen.com |
| Fragrance | Nivamar BM | 0.15 | www.bell-europe.com |

Preparation:
1. Heat phases A and B separately to 80° C.
2. Add phase A to phase B with stirring
3. Allow to cool to 45° C.
4. Add phase C Example 22: Transparent Lipstick

| INCI Name | Product Name | %W/W | Supplier |
|---|---|---|---|
| A | | 100.00 | |
| Ethylenediamine/Hydrogenated Dimer | Sylvaclear A2614V | 28.00 | www.arizonachemical.com |

| INCI Name | Product Name | %W/W | Supplier |
|---|---|---|---|
| Dilinoleate Copolymer Bis-Di-C14-18 Alkyl Amide Bis-Stearyl Ethylenediamine/Neopentyl Glycol/Hydrogenated Dimer Dilinoleate | Sylvaclear C75V | 28.00 | www.arizonachemical.com |
| Paraffinum Liquidum | Paraffinum Liquidum | 13.80 | www.heess.de |
| *Macadamia Integrifolia* Seed Oil | Floramac Hawaiian Macadamia Oil-Refined | ad 100 | www.floratech.com |
| Isopropyl Myristate | Isopropyl Myristate | 6.00 | www.vwr.com |
| C12-15 Alkyl Benzoate | Sympatens-LBZ | 6.00 | www.kolb.ch |
| Caprylic/Capric Triglyceride | Miglyol 812 | 7.00 | www.sasolwax.com |
| Propylparaben | Propyl-4-hydroxybenzoate | 0.20 | www.sigmaaldrich.com |
| B | | | |
| Effect pigment of example 2/3 | — | 0.01-3.50 | |

Preparation:
1. Heat phase A to 85° C.
2. Add phase B to phase A and mix
3. Dispense into lipstick mold at 75° C.

Example 23: Body Lotion Water-In-Silicone

| INCI Name | Product Name | %W/W | Supplier |
|---|---|---|---|
| A | | 100.00 | |
| Cyclopentasiloxane (and) Dimethiconol | Dow Corning 1501 | 11.50 | www.dowcorning.com |
| Cyclopentasiloxane | Dow Corning 245 | 5.75 | www.dowcorning.com |
| Cyclopentasiloxane (and) PEG/PPG-/18/18 Dimethicone | Dow Corning 5225 C | 13.80 | www.dowcorning.com |
| C 30-45 Alkyl Methicone | Dow Corning Cosmetic Wax AMS-C30 | 3.45 | www.dowcorning.com |
| Effect pigment of example 2/3 | — | 0.05-3.50 | |
| C | | | |
| Polysorbate 20 | Tween 20 | 0.60 | www.uniqema.com |
| Phenoxyethanol (and) Methylparaben (and) Ethylparaben (and) Butylparaben | Uniphen P-23 | 0.35 | www.induchem.com |
| Sodium Chloride | Sodium Chloride | 0.75 | www.vwr.com |
| Water | Aqua | ad 100 | |

Preparation:
1. Mix phase A and heat to 75° C.
2. Mix phase B and heat to 70° C.
3. Add phase B slowly to phase A, with homogenization, and allow to cool with stirring

Example 24: Tinted Day Cream

| INCI Name | Product Name | % W/W | Supplier |
|---|---|---|---|
| A | | 100.00 | |
| Mica (and) Titanium Dioxide (and) Iron Oxides | Prestige ® Soft Beige | 1.00 | www.eckart.net |
| Mica (and) Titanium Dioxide | Prestige ® Soft Red | 2.00 | www.eckart.net |
| Effect pigment of example 2/3 | — | 0.05-3.00 | |
| Silica | Syloblanc 34 | 3.00 | www.gracedavision.com |
| Glycerin | Pricerine 9090 | 5.00 | www.uniqema.com |
| Allantoin | Allantoin | 0.40 | www.3v.com |
| Mica | Silk Mica | 3.00 | www.vwr.com |
| Boron Nitride | Boroneige #1501 | 1.50 | www.esk.com |
| Water | | ad 100 | |
| Xanthan Gum | Keltrol T | 0.20 | www.cpkelco.com |
| B | | | |
| Glyceryl Stearate (and) PEG-100 Stearate | Lipomulse 165 | 2.00 | www.lipochemicals.com |
| Ceteryl Alcohol (and) Cetearyl Glucoside | Montanov 68 | 2.20 | www.seppic.com |
| Dimethicone | Dow Corning 200 | 1.00 | www.dowcorning.com |

| INCI Name | Product Name | % W/W | Supplier |
|---|---|---|---|
| | Fluid/350 cst | | |
| Cetearyl Isononanoate | Tego Soft CI | 5.10 | www.degussa.com |
| Octyldodecanol | Eutanol G | 4.00 | www.cognis.com |
| *Butyrospernum Parkii* (Shea Butter) | Shea Butter | 3.80 | www.jandekker.com |
| C | | | |
| Phenoxyethanol (and) Methylparaben (and) Ethylparaben (and) Butylparaben | Uniphen-23 | 0.40 | www.permcos.com |
| Fragrance | Sensuality | 0.10 | www.drom.de |

Preparation:
1. Mix phase A, disperse Keltrol
2. Heat to 80° C.
3. Heat phase B to 80° C.
4. Add phase B slowly to phase A
5. Allow to cool to 40° C., and add phase C

Example 25: Hair Mascara

| INCI Name | Product Name | % W/W | Supplier |
|---|---|---|---|
| A | | 100.00 | |
| Polyquaternium-16 | Luviquat FC 905 (Luviquat Exellence) | 2.70 | www.basf.com |
| Propylene Glycol | 1,2-Propanediol | 1.80 | www.vwr.com |
| Methylparaben | Methyl-4-hydroxybenzoate | 0.20 | www.sigmaaldrich.com |
| Aqua | Water | ad 100 | |
| B | | | |
| Cetearyl Alcohol | Lanette O | 5.00 | www.cognis.com |
| Dimethicone | Dow Corning 200 Fluid/350 cst | 1.00 | www.dowcorning.com |
| Ceteareth-25 | Cremophor A 25 | 2.00 | www.basf.com |
| Propylparaben | Propyl-4-hydroxybenzoate | 0.10 | www.sigmaaldrich.com |
| C | | | |
| Hydroxypropylcellulose | Klucel G | 0.50 | www.herc.com |
| Magnesium Aluminium Silicate | Veegum HV | 0.50 | www.rtvanderbilt.com |
| Aqua | Water | 19.00 | |
| D | | | |
| Effect pigment of example 2/3 | — | 0.10-8.00 | |
| Phenoxyethanol (and) Methylparaban (and) Butylparaben (and) Ethylparaben (and) Propylparaben (and) Isobutylparaben | Phenonip | 0.20 | www.clariant.com |
| Fragrance | Blue Shadow OKO | 0.05 | www.bell-europe.com |

Preparation:
1. Heat phases A and B separately to 80° C.
2. Add phase B slowly to phase A
3. In separate vessel, stir Klucel and Veegum into the water of phase C
4. Allow phase AB to cool to 40° C.
5. Add phases C and D

Example 26: Perfume Powder Stick

| INCI Name | Product Name | % W/W | Supplier |
|---|---|---|---|
| A | | 100.00 | |
| Dimethicone/Vinyl Dimethicone Crosspolymer and Silica | Dow Corning 9701 Cosmetic Powder | ad 100 | www.dowcorning.com |
| Talc | Talc Powder | 29.00 | www.riedeldehaen.com |
| Amorphoeus Silica | Spheron P-1500 | 1.00 | www.cheshamchemicals.co.uk |
| Effect pigment of example 2/3 | — | 0.05-8.00 | |

-continued

| INCI Name | Product Name | % W/W | Supplier |
|---|---|---|---|
| B | | | |
| Fragrance | Moisturadiance | 5.00 | www.drom.com |

Preparation:
1. Mix phase A in speed mixer (30 s/2000 rpm)
2. Add phase B to phase A and mix in speed mixer (30 s/2500 rpm)
3. Dispense into suitable container Example 27: Pressed Blush

| INCI Name | Product Name | % W/W | Supplier |
|---|---|---|---|
| A | | 100.00 | |
| Mica | Silk Mica | ad 100 | www.vwr.com |
| Nylon 12 | Orgasol 2002D/Nat | 3.20 | www.atofinachemicals.com |
| Boron Nitride | Boroneige #1501 | 3.00 | www.esk.com |
| Talc | Talc Powder | 15.00 | www.riedeldehaen.com |
| Zinc Stearate | Kemilub EZ-V | 2.00 | www.undesa.com |
| Effect pigment of example 2/3 | — | 0.05-8.00 | |
| B | | | |
| Octyl Palmitate | Liponate EHP | 8.00 | www.lipochemicals.com |

Preparation:
1. Mix phase A
2. Add phase B and homogenize
3. Press blush at 150 bar for 30 s

What is claimed is:

1. Effect pigments consisting essentially of artificial platelet-shaped substrates which have only one optically active coating comprising $TiO_2$ in the rutile or anatase crystal polymorph, wherein in case of the rutile polymorph, the coating is obtained by a process comprising applying $SnO_2$ to the substrates, applying $TiO_2$ to the applied $SnO_2$, and then calcining the substrates, wherein the effect pigments have a volume-averaged cumulative undersize distribution curve with the characteristic numbers $D_{10}$, $D_{50}$ and $D_{90}$, said cumulative undersize distribution curve having a span $\Delta D$ of 0.7-1.4, and the span $\Delta D$ being calculated in accordance with formula (I):

$$\Delta D = (D_{90} - D_{10})/D_{50} \quad (I),$$

and the average thickness of the artificial platelet-shaped substrates being 500 nm to 2000 nm, wherein the standard deviation of the thickness of the artificial platelet-shaped substrates is 15% to 100%, and wherein the artificial platelet-shaped substrates are substantially transparent and are selected from the group consisting of glass platelets, platelets of synthetic mica, $SiO_2$ platelets, platelet-shaped bismuth oxychloride, platelet-shaped aluminum oxides, and mixtures thereof.

2. The effect pigments of claim 1, wherein the average thickness of the artificial platelet-shaped substrates is 750 nm to 1500 nm.

3. The effect pigments of claim 1, wherein the one optically active coating of the artificial substrates has a refractive index of n≥1.9.

4. Effect pigments consisting essentially of glass platelet-shaped substrates which have only one optically active coating comprising $TiO_2$ in the rutile or anatase crystal polymorph, wherein in case of the rutile polymorph, the coating is obtained by a process comprising applying $SnO_2$ to the substrates, applying $TiO_2$ to the applied $SnO_2$, and then calcining the substrates, wherein the effect pigments have a volume-averaged cumulative undersize distribution curve with the characteristic numbers $D_{10}$, $D_{50}$ and $D_{90}$, said cumulative undersize distribution curve having a span $\Delta D$ of 0.7-1.4, and the span $\Delta D$ being calculated in accordance with formula (I):

$$\Delta D = (D_{90} - D_{10})/D_{50} \quad (I),$$

and the average thickness of the platelet-shaped substrates being 500 nm to 2000 nm.

5. The effect pigments of claim 4, wherein the average thickness of the artificial platelet-shaped substrates is 750 nm to 1500 nm.

6. The effect pigments of claim 4, wherein the standard deviation of the thickness of the artificial substrates is 15% to 100%.

7. The effect pigments of claim 4, wherein the one optically active coating of the artificial substrates has a refractive index of n≥1.9.

8. The effect pigments of claim 4, wherein the average thickness of the artificial platelet-shaped substrates is 750 nm to 1500 nm and the standard deviation of the thickness of the artificial substrates is 20% to 70%.

9. The effect pigments of claim 4, wherein the average thickness of the artificial platelet-shaped substrates is 750 nm to 1500 nm the span $\Delta D$ is within a range of 0.8 to 1.2.

10. The effect pigments of claim 1, wherein the standard deviation of the thickness of the artificial platelet-shaped substrates is in a range of 15% to 70%.

11. The effect pigments of claim 1, wherein the standard deviation of the thickness of the artificial platelet-shaped substrates is in a range of 20% to 70%.

12. The effect pigments of claim 1, wherein the standard deviation of the thickness of the artificial platelet-shaped substrates is in a range of 15% to 70%, and wherein the average thickness of the substrate is 750 nm to 1500 nm.

13. The effect pigments of claim 1, wherein the standard deviation of the thickness of the artificial platelet-shaped substrates is in a range of 20% to 70%, and wherein the average thickness of the substrate is 750 nm to 1500 nm.

14. The effect pigments of claim 4, wherein the average thickness of the artificial platelet-shaped substrates is 750 nm to 1500 nm, and wherein the standard deviation of the thickness of the artificial substrates is 15% to 70%.

* * * * *